United States Patent
Kwon et al.

(10) Patent No.: US 11,180,754 B2
(45) Date of Patent: *Nov. 23, 2021

(54) POLYPEPTIDE AND METHOD OF PRODUCING IMP USING THE SAME

(71) Applicant: CJ CHEILJEDANG CORPORATION, Seoul (KR)

(72) Inventors: Jung Gun Kwon, Gimpo-si (KR); Min Ji Baek, Suwon-si (KR); Ji Hye Lee, Anyang-si (KR); Nara Kwon, Yongin-si (KR); Ju Jeong Kim, Suwon-si (KR); Jin Ah Rho, Suwon-si (KR); Jin Man Cho, Seongnam-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/425,897

(22) Filed: May 29, 2019

(65) Prior Publication Data
US 2019/0284595 A1    Sep. 19, 2019

Related U.S. Application Data

(63) Continuation of application No. 16/346,041, filed as application No. PCT/KR2018/015937 on Dec. 14, 2018.

(30) Foreign Application Priority Data

Dec. 15, 2017  (KR) .................. 10-2017-0173505

(51) Int. Cl.
| | |
|---|---|
| *C12N 15/12* | (2006.01) |
| *C12N 15/11* | (2006.01) |
| *C07K 14/34* | (2006.01) |
| *C07K 14/705* | (2006.01) |
| *C12N 1/20* | (2006.01) |
| *C12P 19/32* | (2006.01) |
| *C12N 15/77* | (2006.01) |
| *C12R 1/15* | (2006.01) |

(52) U.S. Cl.
CPC .............. *C12N 15/11* (2013.01); *C07K 14/34* (2013.01); *C07K 14/705* (2013.01); *C12N 1/205* (2021.05); *C12N 15/77* (2013.01); *C12P 19/32* (2013.01); *C12R 2001/15* (2021.05)

(58) Field of Classification Search
None
See application file for complete search history.

(56) References Cited

U.S. PATENT DOCUMENTS

| | | |
|---|---|---|
| 7,767,626 B2 | 8/2010 | Toriyabe et al. |
| 9,271,500 B2 | 3/2016 | Takahashi et al. |
| 9,783,509 B2 | 10/2017 | Alig et al. |
| 9,802,930 B1 | 10/2017 | Tanabe et al. |
| 9,924,719 B2 | 3/2018 | Tanabe et al. |
| 10,039,282 B2 | 8/2018 | Kohler et al. |

FOREIGN PATENT DOCUMENTS

| | | |
|---|---|---|
| EP | 3 608 410 A1 | 2/2020 |
| JP | 2-88570 A | 3/1990 |
| KR | 2003-0042972 A | 6/2003 |
| KR | 10-2007-0060207 A | 6/2007 |
| KR | 10-2007-0060208 A | 6/2007 |
| KR | 10-2010-0109732 A | 10/2010 |
| KR | 10-1744958 B1 | 6/2017 |
| WO | 99/55668 A1 | 11/1999 |
| WO | 2010/100189 A1 | 9/2010 |
| WO | 2013/191113 A1 | 12/2013 |
| WO | 2015/004028 A1 | 1/2015 |
| WO | 2015/091267 A1 | 6/2015 |
| WO | 2016/052247 A1 | 4/2016 |
| WO | 2016/052455 A1 | 4/2016 |

OTHER PUBLICATIONS

Ishii et al., "Improved Inosine Production and Derepression of Purine Nucleotide Biosynthetic Enzymes in 8-Azaguanine Resistant Mutants of Bacillus subtilis," Agr. Biol. Chem. 36(9):1511-1522 (1972).
Mori et al., "A novel process of inosine 5'-monophosphate production using overexpressed guanosine/inosine kinase," Appl Microbiol Biotechnol, 48:693-698, 1997, 6 pages.
NCBI Reference Sequence WP_066795119.1, retrieved from https://www.ncbi.nlm.nih.gov/protein/1055045151/ on May 23, 2019.
NCBI Reference Sequence WP_066795121.1, retrieved from https://www.ncbi.nhn.nih.gov/protein/WP_066795121.1/ on May 24, 2019.
Peifer et al., "Metabolic engineering of the purine biosynthetic pathway in Corynebacterium glutamicum results in increased intracellular pool sizes of IMP and hypoxanthine," Microbial Cell Factories, 11:138, 2012, 14 pages.
GenBank: ASJ19118.1, "transcriptional regulator [Corynebacterium stationis]," (two pages) Jul. 5, 2017.
MFS transporter [Corynebacterium stationis]—GenBank: AMJ44984.1, Feb. 16, 2016.
Kisselev, "Polypeptide Release Factors in Prokaryotes and Eukaryotes: Same Function, Different Structure," *Structure* 10:8-9 (2002).
Whisstock et al., "Prediction of protein function from protein sequence and structure," *Quarterly Reviews of Biophysics* 36(3):307-340 (2003).
Witkowski et al., "Conversion of a β-Ketoacyl Synthase to a Malonyl Decarboxylase by Replacement of the Active-Site Cysteine with Glutamine," *Biochemistry* 38:11643-11650 (1999).
GenBank Accession No. AB0675, probable multidrug efflux STY1517 [imported] *Salmonella enterica* subsp. enterica serovar Typhi (strain CT18) 2 pages, Nov. 18, 2002.
Parkhill et al., "Complete genome sequence of a multiple drug resistant *Salmonella enterica* serovarTyphi CT18," *Nature* 413:848-852 (2001).

(Continued)

*Primary Examiner* — Michael D Pak
(74) *Attorney, Agent, or Firm* — Seed IP Law Group LLP

(57) ABSTRACT

The present disclosure relates to a novel polypeptide having an activity of exporting 5'-inosine monophosphate, a microorganism comprising the same, a method for preparing 5'-inosine monophosphate using the same, and a method for increasing export of 5'-inosine monophosphate.

2 Claims, No Drawings

Specification includes a Sequence Listing.

(56) References Cited

OTHER PUBLICATIONS

Adrio et al., "Genetic improvement of processes yielding microbial products," *FEMS Microbiol Rev* 30:187-214 (2006).
Ledesma-Amaro et al., "Biotechnological production of feed nucleotides by microbial strain improvement," *Process Biochemistry*, http://dx.doi.org/10.1016/j.procbio.2013.06.025, 8 pages (2013).
Sanchez et al., "Metabolic regulation and overproduction of primary metabolites," *Microbiol Biotechnology* 1(4):283-319 (2008).

POLYPEPTIDE AND METHOD OF PRODUCING IMP USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_440C1_SEQUENCE_LISTING.txt. The text file is 70 KB, was created on May 29, 2019, and is being submitted electronically via EFS-Web.

TECHNICAL FIELD

The present disclosure relates to a novel protein variant having an activity of exporting 5'-inosine monophosphate (IMP), a microorganism comprising the same, and a method for preparing IMP and a method for increasing export of IMP using the same.

BACKGROUND ART

5'-Inosine monophosphate (hereinafter, IMP), a nucleic acid material, is an intermediate of the nucleic acid metabolism pathway and is used in many fields such as foods, medicines, various medical applications, etc. In particular, IMP is widely used as an additive for food seasonings or foods, along with 5'-guanine monophosphate (hereinafter, GMP). Although IMP itself is known to provide a beef taste, it is known to enhance the flavor of monosodium glutamic acid (MSG) and is thus attracting attention as a taste-enhancing nucleic acid-based seasoning.

Examples of methods for producing IMP include a method of enzymatically degrading ribonucleic acid extracted from yeast cells (Japanese Patent Publication No. 1614/1957), a method for chemically phosphorylating inosine produced by fermentation (Agri. Biol. Chem., 36, 1511, etc.), a method for culturing microorganisms which can directly produce IMP and recovering IMP in the culture broth, etc. Among these, the method most frequently used at present is a method using microorganisms capable of directly producing IMP.

Meanwhile, since enzymes do not always exhibit optimal properties in nature with respect to activity, stability, substrate specificity for optical isomers, etc. required in industrial applications, various attempts have been made to improve enzymes to suit the intended use by modification of their amino acid sequences, etc. Among these, although rational design and site-directed mutagenesis of enzymes have been applied to improve enzyme function, in many cases, these attempts were shown to be disadvantageous in that information on the structure of target enzymes is not sufficient or the structure-function correlation is not clear, thus preventing their effective application. Additionally, a method of improving enzyme activity by attempting the enhancement of enzymes through directed evolution, which is for screening enzymes of desired traits from a library of modified enzymes constructed through random mutagenesis of enzyme genes, was previously reported.

DISCLOSURE

Technical Problem

In order to produce IMP in high yield using the method of directly producing IMP through microbial fermentation, the IMP should be smoothly exported. To accomplish such object, the inventors of the present disclosure have discovered the protein involved in the activity of exporting IMP, and also have made many efforts to increase IMP production. As a result, they have discovered protein variants having the activity of exporting IMP, thereby completing the present disclosure.

Technical Solution

An object of the present disclosure is to provide a protein variant having the activity of exporting IMP.

Another object of the present disclosure is to provide a polynucleotide encoding the protein variant of the present disclosure.

Still another object of the present disclosure is to provide a vector including the polynucleotide of the present disclosure.

Still another object of the present disclosure is to provide a microorganism producing IMP, including the protein variant and vector of the present disclosure.

Still another object of the present disclosure is to provide a method for preparing IMP, including culturing the microorganism of the present disclosure in a medium.

Still another object of the present disclosure is to provide a method for increasing the export of IMP, including enhancing activity of the protein variant of the present disclosure, which has the activity of exporting IMP.

Advantageous Effects of the Invention

IMP can be produced in high yield by culturing a microorganism of the genus *Corynebacterium* producing IMP using the protein variant of the present disclosure, which is capable of exporting IMP.

BEST MODE FOR CARRYING OUT THE INVENTION

The present disclosure will be described in detail as follows. Meanwhile, each of the explanations and exemplary embodiments disclosed herein can be applied to other respective explanations and exemplary embodiments. That is, all of the combinations of various factors disclosed herein belong to the scope of the present disclosure. Additionally, the scope of the present disclosure should not be limited by the specific disclosure provided hereinbelow.

To achieve the above objects, an aspect of the present disclosure provides a protein variant having an activity of exporting IMP.

As used herein, the term "a protein that exports 5'-inosine monophosphate (IMP)" refers to a protein involved in the extracellular export of IMP. For the purpose of the present disclosure, the term may be used interchangeably with a protein having an activity of exporting IMP, an IMP export protein, a protein having an activity of exporting 5'-inosine monophosphate, a 5'-inosine monophosphate-exporting protein, etc.; specifically, the protein may be expressed as ImpE, and more specifically, may be expressed as ImpE1 or ImpE2, but is not limited thereto. Additionally, the protein may be derived from a microorganism of the genus *Corynebacterium*, and specifically from *Corynebacterium stationis*, but the microorganism is not limited thereto.

The protein, for example, may consist of the amino acid sequence represented by SEQ ID NO: 1 or SEQ ID NO: 2, but any sequence having the same activity as the protein can be included without limitation, and one of ordinary skill in the art can obtain sequence information from GenBank of NCBI, a well-known database. Additionally, the protein may include the amino acid sequence of SEQ ID NO: 1 or SEQ ID NO: 2, or an amino acid sequence having a homology or identity to the sequence of SEQ ID NO: 1 or SEQ ID NO: 2 of at least 80%, at least 90%, at least 95%, at least 96%, at least 97%, at least 98%, or at least 99%. Additionally, it is obvious that any protein having an amino acid sequence with deletion, modification, substitution, or addition in part of the sequence can also be included in the scope of the present disclosure, as long as the amino acid sequence has a homology or identity described above and has an effect corresponding to that of the protein.

That is, although described as "a protein having an amino acid sequence of a particular SEQ ID NO" or "a protein consisting of an amino acid sequence of a particular SEQ ID NO" in the present disclosure, the protein may have an activity that is identical or corresponding to that of a protein consisting of an amino acid sequence of the corresponding SEQ ID NO. In such a case, it is obvious that any proteins having an amino acid sequence with deletion, modification, substitution, conservative substitution, or addition in part of the sequence also can be used in the present disclosure. For example, in the case of having the activity that is the same as or corresponding to that of the modified protein, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it obviously belongs to the scope of the present disclosure.

As used herein, the term "homology" or "identity" refers to a degree of matching with two given amino acid sequences or nucleotide sequences, and may be expressed as a percentage.

The terms "homology" and "identity" may often be used interchangeably with each other.

The sequence homology or identity of conserved polynucleotide or polypeptide sequences may be determined by standard alignment algorithms and can be used with a default gap penalty established by the program being used. Substantially homologous or identical sequences are generally expected to hybridize under moderate or high stringency, along the entire length or at least about 50%, about 60%, about 70%, about 80%, or about 90% of the entire length of the sequences. Polynucleotides that contain degenerate codons instead of codons in the hybridizing polypeptides are also considered.

Whether any two polynucleotide or polypeptide sequences have a homology, similarity, or identity may be determined using a known computer algorithm such as the "FASTA" program (Pearson et al., (1988) [Proc. Natl. Acad. Sci. USA 85]: 2444: using default parameters in 2444). Alternately, it may be determined using the Needleman-Wunsch algorithm (Needleman and Wunsch, 1970, J. Mol. Biol. 48: 443-453), which is performed in the Needleman program of the EMBOSS package ((EMBOSS: The European Molecular Biology Open Software Suite, Rice et al., 2000, Trends Genet. 16: 276-277) (version 5.0.0 or versions thereafter) (GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48: 1073). For example, the homology, similarity, or identity may be determined using BLAST or ClustalW of the National Center for Biotechnology Information (NCBI).

The homology, similarity, or identity of polynucleotide or polypeptide sequences may be determined by comparing sequence information using, for example, the GAP computer program (e.g., Needleman et al., (1970), J Mol Biol. 48: 443) as published (e.g., Smith and Waterman, Adv. Appl. Math (1981) 2:482). In summary, the GAP program defines the homology, similarity, or identity as the value obtained by dividing the number of similarly aligned symbols (i.e., nucleotides or amino acids) into the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to relevance between sequences. Specifically, the protein variant of the present disclosure having the activity of exporting IMP may be one in which at least one amino acid selected from the group consisting of the $164^{th}$ amino acid in the amino acid sequence of SEQ ID NO: 1, the $222^{nd}$ amino acid in the amino acid sequence of SEQ ID NO: 1, the $2^{nd}$ amino acid in the amino acid sequence of SEQ ID NO: 2, and the $64^{th}$ amino acid in the amino acid sequence of SEQ ID NO: 2 is substituted with another amino acid, but is not limited thereto.

For example, in the protein variant having the activity of exporting IMP, the $164^{th}$ amino acid in the amino acid sequence of SEQ ID NO: 1 is substituted with lysine, arginine, asparagine, glycine, threonine, or proline; the $2^{nd}$ amino acid in the amino acid sequence of SEQ ID NO: 2 is substituted with isoleucine, phenylalanine, methionine, glutamic acid, histidine, or asparagine; or the $64^{th}$ amino acid in the amino acid sequence of SEQ ID NO: 2 is substituted with aspartic acid, glutamic acid, asparagine, cysteine, isoleucine, or phenylalanine, but is not limited thereto.

As a specific example, the protein variant having the activity of exporting IMP may be a protein having the amino acid sequence consisting of SEQ ID NO: 141, 142, 145, 147, 149, or 151, a protein having an amino acid sequence encoded by the polynucleotide of SEQ ID NO: 153 or 154, or a protein having an amino acid sequence having a homology thereto of at least 80%, at least 90%, at least 95%, at least 96%, at least 97%, at least 98%, or at least 99%. In addition, it is apparent that a protein having a deletion, modification, substitution, or addition of some sequence may be used as the protein of the present disclosure as long as it is a protein having the amino acid sequence with the homology above and exhibiting an effect corresponding to that of the protein.

Another aspect of the present disclosure provides a polynucleotide encoding the protein variant, or a vector including the polynucleotide.

As used herein, the term "polynucleotide" refers to a polymer of nucleotides which is extended in a long chain by covalent bonds and has a DNA strand or an RNA strand longer than a certain length, and more specifically, refers to a polynucleotide fragment encoding the protein variant.

It is apparent that a polynucleotide, which can be translated by codon degeneracy into a protein consisting of the amino acid sequence of SEQ ID NO: 141, 142, 145, 147, 149, or 151, a protein consisting of an amino acid sequence encoded by the polynucleotide of SEQ ID NO: 153 or 154, or into a protein having a homology thereto, also can be included as the polynucleotide of the present disclosure. For example, the polynucleotide of the present disclosure may be a polynucleotide having a nucleotide sequence of SEQ ID NO: 143, 144, 146, 148, 150, 152, 153, or 154, and more specifically, may be a polynucleotide composed of a nucleotide sequence of SEQ ID NO: 143, 144, 146, 148, 150, 152, 153, or 154. In addition, a polynucleotide sequence, which encodes a protein having the activity of the protein consisting of an amino acid sequence of SEQ ID NO: 141, 142, 145, 147, 149, or 151 or an amino acid sequence encoded by a polynucleotide of SEQ ID NO: 153 or 154 by hybridization under stringent conditions with a probe which can be prepared from known gene sequences, e.g., a complementary sequence to all or part of the nucleotide sequence, may be included without limitation.

The term "stringent conditions" refers to conditions under which specific hybridization between polynucleotides is made possible. Such conditions are specifically described in references (e.g., J. Sambrook et al., supra). For example, the conditions may include performing hybridization between genes having a high homology, a homology of 40% or higher, specifically 90% or higher, more specifically 95% or higher, even more specifically 97% or higher, and most specifically 99% or higher, while not performing hybridization between genes having a homology of lower than the above homologies; or to perform hybridization once, specifically two or three times, under conventional washing conditions for southern hybridization of 60° C., 1×SSC, and 0.1% SDS, specifically at a salt concentration and temperature corresponding to 60° C., 0.1×SSC, and 0.1% SDS, and more specifically 68° C., 0.1×SSC, and 0.1% SDS.

Hybridization requires that two nucleic acids have a complementary sequence, although mismatches between bases may be possible depending on the stringency of the hybridization. The term "complementary" is used to describe the relationship between mutually hybridizable nucleotide bases. For example, with respect to DNA, adenosine is complementary to thymine, and cytosine is complementary to guanine. Accordingly, the present disclosure may also include isolated nucleic acid fragments complementary to the entire sequence as well as substantially similar nucleic acid sequences.

Specifically, polynucleotides having a homology can be detected at a Tm value of 55° C. using hybridization conditions that include a hybridization step and using the conditions described above. Additionally, the Tm value may be 60° C., 63° C., or 65° C., but is not limited thereto and may be appropriately adjusted by an ordinary person skilled in the art according to the intended purpose.

The stringency suitable for the hybridization of polynucleotides depends on the length and complementarity of the polynucleotides and the related variables are well known in the art (see Sambrook et al., supra, 9.50 to 9.51 and 11.7 to 11.8).

As used herein, the term "vector" refers to a DNA construct including the nucleotide sequence of the polynucleotide encoding a target protein, in which the target protein is operably linked to a suitable control sequence so that the target protein can be expressed in an appropriate host. The control sequence may include a promoter capable of initiating transcription, any operator sequence for controlling the transcription, a sequence encoding an appropriate mRNA ribosome-binding domain, and a sequence controlling the termination of transcription and translation. The vector, after being transformed into a suitable host cell, may be replicated or function irrespective of the host genome, or may be integrated into the host genome itself.

The vector used in the present disclosure may not be particularly limited as long as the vector is replicable in the host cell, and it may be constructed using any vector known in the art. Examples of the vector may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used; and as a plasmid vector, those based on pBR, pUC, pBluescriptII, pGEM, pTZ, pCL, pET, etc. may be used. Specifically, pDZ, pACYC177, pACYC184, pCL, pECCG117, pUC19, pBR322, pMW118, pCC1BAC vectors, etc. may be used.

In an embodiment, the polynucleotide encoding the target protein may be replaced with a modified polynucleotide within the chromosome using a vector for the insertion into the chromosome in a cell. The insertion of the polynucleotide into the chromosome may be performed using a known method in the art, for example, by homologous recombination, but is not limited thereto. In particular, a selection marker for confirming the insertion into the chromosome may be further included. The selection marker is used for selection of a transformed cell, i.e., in order to confirm whether the target nucleic acid has been inserted, and markers capable of providing selectable phenotypes such as drug resistance, nutrient requirement, resistance to cytotoxic agents, and expression of surface proteins may be used. Under the circumstances where selective agents are treated, only the cells capable of expressing the selection markers can survive or express other phenotypic traits, and thus the transformed cells can be easily selected.

Still another aspect of the present disclosure provides a microorganism producing IMP, including the protein variant of the present disclosure, the polynucleotide of the present disclosure encoding the protein variant, or the vector of the present disclosure. Specifically, the microorganism including the protein variant and/or a polynucleotide encoding the protein variant may be a microorganism prepared by transformation using a vector containing the polynucleotide encoding the protein variant, but the microorganism is not limited thereto.

As used herein, the term "transformation" refers to a process of introducing a vector including a polynucleotide encoding a target protein into a host cell, thereby enabling the expression of the protein encoded by the polynucleotide in the host cell. For the transformed polynucleotide, it does not matter whether it is inserted into the chromosome of the host cell and located therein or located outside the chromosome, as long as the transformed polynucleotide can be expressed in the host cell. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all of the essential elements required for self-expression. The expression cassette may conventionally include a promoter operably linked to the polynucleotide, a transcription termination signal, a ribosome-binding domain, and a translation termination signal. The expression cassette may be in the form of a self-replicable expression vector. Additionally, the polynucleotide may be introduced into a host cell as is and operably linked to a sequence essential for its expression in the host cell, but is not limited thereto.

Additionally, as used herein, the term "operably linked" refers to a functional linkage between a promoter sequence, which initiates and mediates the transcription of the polynucleotide encoding the target protein, i.e., a conjugate of the present disclosure, and the above gene sequence.

As used herein, the term "IMP-producing microorganism" refers to a microorganism which is naturally capable of producing IMP; or a microorganism introduced an ability to produce or export IMP to whose parent strain is not naturally capable of producing and/or exporting IMP which is In the present disclosure, the microorganism producing IMP can be used interchangeably with a microorganism having an activity of exporting IMP.

The IMP-producing microorganism is a cell or microorganism which includes a protein variant having an activity of exporting IMP or a polynucleotide encoding the protein variant, or which is transformed with a vector containing the polynucleotide encoding the protein variant, and is thereby capable of expressing the protein variant. For the purposes of the present disclosure, the host cell of the IMP-producing microorganism or microorganism may be any microorganism including the protein variant thus capable of producing IMP. For example, the microorganism may be a microorganism of the genus *Escherichia*, a microorganism of the genus *Serratia*, a microorganism of the genus *Erwinia*, a microorganism of the genus Enterobacteria, a microorganism of the genus *Salmonella*, a microorganism of the genus *Streptomyces*, a microorganism of the genus *Pseudomonas*, a microorganism of the genus *Brevibacterium*, a microorganism of the genus *Corynebacterium*, etc., and specifically, a microorganism of the genus *Corynebacterium*.

As used herein, the term "IMP-producing microorganism of the genus *Corynebacterium*" refers to a microorganism of the genus *Corynebacterium* which is naturally capable of producing IMP or capable of producing IMP by modification. Specifically, as used herein, the microorganism of the genus *Corynebacterium* capable of producing IMP refers to a native strain of the microorganism of the genus *Corynebacterium* capable of producing IMP; or a microorganism of the genus *Corynebacterium* with enhanced abilities to produce IMP prepared by inserting a gene associated with IMP production or by enhancing or attenuating the endogenous gene associated with IMP production. More specifically, in the present disclosure, the microorganism of the genus *Corynebacterium* capable of producing IMP refers to a microorganism of the genus *Corynebacterium* which has improved abilities to produce IMP by including a protein variant having an activity of exporting IMP or a polynucleotide encoding the protein variant, or by being transformed with a vector containing the polynucleotide encoding the protein variant. The "microorganism of the genus *Corynebacterium* with enhanced abilities to produce IMP" refers to a microorganism of the genus *Corynebacterium* with improved abilities to produce IMP compared to that of its parent strain before transformation or that of an unmodified microorganism of the genus *Corynebacterium*. The "unmodified microorganism of the genus *Corynebacterium*" refers to a native type of the microorganism of the genus *Corynebacterium*, a microorganism of the genus *Corynebacterium* which does not contain a protein variant capable of exporting IMP, or a microorganism of the genus *Corynebacterium* which is not transformed with a vector containing a polynucleotide encoding the protein variant capable of exporting IMP.

In an embodiment of the present disclosure, the microorganism of the present disclosure may be a microorganism of the genus *Corynebacterium*, in which the activity of adenylosuccinate synthetase and/or IMP dehydrogenase is further attenuated.

In the present disclosure, "a microorganism of the genus *Corynebacterium*" specifically refers to *Corynebacterium glutamicum, Corynebacterium ammoniagenes, Brevibacterium lactofermentum, Brevibacterium flavum, Corynebacterium thermoaminogenes, Corynebacterium efficiens, Corynebacterium stationis*, etc., but the microorganism is not necessarily limited thereto.

Still another aspect of the present disclosure provides a method for preparing IMP, including culturing the microorganism of the genus *Corynebacterium* in a medium.

Specifically, the method of the present disclosure may additionally include a step of recovering IMP from the microorganism or medium.

In the above method, the cultivation of the microorganism may be performed in a batch process, continuous process, fed-batch process, etc. known in the art, but the cultivation process is not particularly limited thereto. In particular, with respect to the cultivation conditions, the pH of the culture may be adjusted to a suitable pH (e.g., pH 5 to 9, specifically pH 6 to 8, and most specifically with an appropriate basic compound (e.g., sodium hydroxide, potassium hydroxide, or ammonia) or acidic compound (e.g., phosphoric acid or sulfuric acid), and the aerobic condition of the culture may be maintained by introducing oxygen or an oxygen-containing gas mixture to the culture. The cultivation temperature may generally be in the range of 20° C. to 45° C., and specifically 25° C. to 40° C. for about 10 to 160 hours, but the cultivation conditions are not limited thereto. The IMP produced by the above cultivation may be secreted into the culture or may be retained in the cells.

Additionally, examples of the carbon sources to be used in the culture medium may include sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid), but are not limited thereto. These carbon sources may be used alone or in combination, but are not limited thereto. Examples of the nitrogen sources to be used in the culture medium may include nitrogen-containing organic compounds (e.g., peptone, yeast extract, meat gravy, malt extract, corn steep liquor, soybean flour, and urea) or inorganic compounds (e.g., ammonium sulfate, ammonium chloride, ammonium phosphate, ammonium carbonate, and ammonium nitrate), etc. These nitrogen sources may be used alone or in combination, but are not limited thereto. Examples of the phosphorus sources to be used in the culture medium may include potassium dihydrogen phosphate, dipotassium hydrogen phosphate, corresponding sodium-containing salts, etc., but are not limited thereto. Additionally, metal salts (e.g., magnesium sulfate or iron sulfate), amino acids, vitamins, etc., which are essential growth-promoting materials, may be contained in the medium.

In the present disclosure, the method for recovering the IMP produced in the step of cultivation may be performed by collecting the IMP from the culture broth using an appropriate method known in the art. For example, methods such as centrifugation, filtration, anion exchange chromatography, crystallization, HPLC, etc. may be used, and the desired IMP can be recovered from a culture or cultured microorganism using an appropriate method known in the art.

Further, the recovery may include a purification process and may be performed using an appropriate method known in the art. Thus, the IMP to be recovered may be in a purified form or a microorganism fermentation broth containing IMP.

Still another aspect of the present disclosure provides a composition for producing IMP, including the protein variant of the present disclosure, which has the activity of exporting IMP, or a polynucleotide encoding the same.

The composition of the present disclosure may further include, without limitation, a constitution capable of operating the polynucleotide. In the composition of the present disclosure, the polynucleotide may be in a form included within a vector to express an operably linked gene in the introduced host cell.

Additionally, the composition may further include any suitable excipients conventionally used in the composition for producing IMP. Such excipients may be, for example, preservatives, humectants, suspending agents, buffers, stabilizing agents, or isotonic agents, but are not limited thereto.

Still another aspect of the present disclosure provides use of the protein of the present disclosure for increasing the production of IMP in the microorganism of the genus *Corynebacterium*.

Still another aspect of the present disclosure provides a method for increasing the export of IMP, including enhancing the activity of the protein variant, which has the activity of exporting IMP, in the microorganism of the genus *Corynebacterium*.

The terms "protein having the activity of exporting IMP", "enhancement", and "microorganism of the genus *Corynebacterium*" are as described above.

Still another aspect of the present disclosure provides use of the protein of the present disclosure for increasing the export of IMP in the microorganism of the genus *Corynebacterium*.

DETAILED DESCRIPTION OF THE EMBODIMENT

Hereinafter, the present disclosure will be described in detail through exemplary embodiments. However, it should be obvious to one of ordinary skill in the art that these exemplary embodiments are provided for the purpose of illustration only and are not intended to limit the scope of the present disclosure.

Example 1: Discovery of IMP Export Proteins

A genomic DNA library of *Corynebacterium stationis* ATCC6872 was prepared for the identification of membrane proteins of *Corynebacterium* involved in the export of IMP. Then, since the wild-type strain of *Corynebacterium* cannot produce IMP, or even if it does produce IMP, it produces only a small amount thereof, a strain called CJI0323, which is capable of producing IMP, derived from the ATCC6872 strain was prepared for the identification of the ability to produce IMP. The CJI0323 strain prepared was subjected to screening of membrane proteins involved in IMP export using the genomic DNA library of the ATCC6872 strain. The specific details of the experiment are as follows.

Example 1-1: Selection of IMP-Producing Strain, CJI0323

The ATCC6872 cells were suspended in a phosphate buffer (pH 7.0) or citrate buffer (pH 5.5) at a concentration of $10^7$ cells/mL to $10^8$ cells/mL to prepare an ATCC6872-derived IMP-producing strain, and the cells were subjected to UV treatment to induce mutation. The resulting cells were washed twice with a 0.85% saline solution, and then diluted and plated on a medium, which was prepared by adding a resistance-providing material at an appropriate concentration to a minimal medium containing 1.7% agar, and colonies were obtained thereafter. Each colony was cultured in a nutrient medium and cultured in a seed medium for 24 hours. After culturing the colonies for 3 to 4 days in a fermentation medium, the colony with the highest abilities to produce IMP accumulated in the culture medium was selected. In the course of preparing a strain capable of producing IMP at high concentration, in order to provide adenine auxotrophy, guanine leakage, lysozyme susceptibility, 3,4-dihydroproline resistance, streptomycin resistance, azetidine carboxylic acid resistance, thiaproline resistance, azaserine resistance, sulfaguanidine resistance, norvaline resistance, and trimethoprim resistance, the procedures above were performed sequentially for each material. As a result, CJI0323, which showed resistance to the above materials and excellent abilities to produce IMP, was finally selected. The degree of resistance between ATCC6872 and CJI0323 was compared and the results are shown in Table 1 below.

TABLE 1

| Characteristics | ATCC6872 | CJI0323 |
|---|---|---|
| Adenine auxotrophy | Non-auxotrophy | Auxotrophy |
| Guanine leakage | Non-auxotrophy | Leaky auxotrophy |
| Lysozyme susceptibility | 80 μg/mL | 8 μg/mL |
| 3,4-Dihydroproline resistance | 1000 μg/mL | 3500 μg/mL |
| Streptomycin resistance | 500 μg/mL | 2000 μg/mL |
| Azetidine carboxylic acid resistance | 5 mg/mL | 30 mg/mL |
| Thiaproline resistance | 10 μg/mL | 100 μg/mL |
| Azaserine resistance | 25 μg/mL | 100 μg/mL |
| Sulfaguanidine resistance | 50 μg/mL | 200 μg/mL |
| Norvaline resistance | 0.2 mg/mL | 2 mg/mL |
| Trimethoprim resistance | 20 μg/mL | 100 μg/mL |

Minimal medium: 2% glucose, 0.3% sodium sulfate, 0.1% $KH_2SO_4$, 0.3% $K_2HPO_4$, 0.3% magnesium sulfate, calcium chloride (10 mg/L), iron sulfate (10 mg/L), zinc sulfate (1 mg/L), manganese chloride (3.6 mg/L), L-cysteine (20 mg/L), calcium pantothenate (10 mg/L), thiamine hydrochloride (5 mg/L), biotin (30 μg/L), adenine (20 mg/L), guanine (20 mg/L), pH 7.3

Nutrient medium: 1% peptone, 1% meat juice, 0.25% sodium chloride, 1% yeast extract, 2% agar, pH 7.2

Seed medium: 1% glucose, 1% peptone, 1% meat juice, 1% yeast extract, 0.25% sodium chloride, adenine (100 mg/L), guanine (100 mg/L), pH 7.5

Fermentation medium: 0.1% sodium glutamate, 1% ammonium chloride, 1.2% magnesium sulfate, 0.01% calcium chloride, iron sulfate (20 mg/L), manganese sulfate (20 mg/L), zinc sulfate (20 mg/L), copper sulfate (5 mg/L), L-cysteine (23 mg/L), alanine (24 mg/L), nicotinic acid (8 mg/L), biotin (45 μg/L), thiamine hydrochloride (5 mg/L), adenine (30 mg/L), 1.9% phosphoric acid (85%), 2.55% glucose, 1.45% fructose

Example 1-2: Experiments on Fermentation Titer of CJI0323

The seed medium (2 mL) was dispensed into test tubes (diameter: 18 mm), which were then autoclaved and each inoculated with ATCC6872 and CJI0323. Thereafter, the resultants were shake-cultured at 30° C. for 24 hours and then used as a seed culture solution. The fermentation medium (29 mL) was dispensed into Erlenmeyer flasks (250 mL) for shaking, autoclaved at 121° C. for 15 minutes, and the seed culture solution (2 mL) was inoculated thereto and cultured for 3 days. The culture conditions were set to 170 rpm, 30° C., and a pH of 7.5.

Upon completion of the culture, the amount of IMP produced was measured by HPLC (SHIMAZDU LC20A) and the results of the culture are shown in Table 2 below.

TABLE 2

| Strain | IMP (g/L) |
|---|---|
| ATCC6872 | 0 |
| CJI0323 | 9.52 |

The CJI0323 strain was named as *Corynebacterium stationis* CN01-0323. The strain was deposited under the Budapest Treaty to the Korean Culture Center of Microorganisms (KCCM) on Nov. 7, 2017. In addition, the strain was designated as Accession No. KCCM12151P.

Example 1-3: Discovery of Exporting Proteins

Screening conditions showing growth inhibition of the CJI0323 strain were established by additionally adding IMP to the minimal medium containing 1.7% agar. The plasmids of the genomic library of the ATCC6872 strain were transformed into the CJI0323 strain by electroporation (van der Rest et al. 1999), and those colonies in which the growth inhibition was released under the medium conditions supplemented with an excess amount of IMP were selected. Plasmids were obtained from the selected colonies and analyzed by a sequencing technique. As a result, one kind of membrane protein involved in the release of the growth inhibition was identified under the condition where an excess amount of IMP was added.

The one kind of membrane protein from *Corynebacterium* was identified based on the amino acid sequence of SEQ ID NO: 2 and the nucleotide sequence of SEQ ID NO: 4 (NCBI GenBank: NZ_CP014279, WP_066795121, MFS transporter). The membrane protein is known as the MFS transporter, but its specific function has not been confirmed, and further, its function regarding the IMP export is still unknown. In the present disclosure, the membrane protein was named ImpE2(WT).

Example 2: Identification of ImpE1 and ImpE2

Example 2-1: Confirmation of impE1 and impE2

In order to examine the functions of the membrane protein, ImpE2, the gene structure of SEQ ID NO: 4 was confirmed in the NCBI (NCBI GenBank: NZ_CP014279, WP_066795121, MFS transporter). As a result, it was confirmed that the 7 bp starting portion of the ORF of SEQ ID NO: 4 (impE2) overlaps in 7 bp with a different gene (NCBI GenBank: NZ_CP014279, WP_066795119, transcriptional regulator), which is located upstream of impE2. Since the functions of the gene located upstream of impE2 and the protein encoded by the gene have not been confirmed, in the present disclosure, the protein was named ImpE1(WT) (the amino acid sequence of SEQ ID NO: 1 and the nucleotide sequence of SEQ ID NO: 3).

Example 2-2: Preparation of impE1- or impE2-Deficient Vector

In order to confirm whether the deletion of ImpE1 or ImpE2, which are involved in releasing the growth inhibition caused by IMP as identified in Examples 1 and 2-1, in an IMP-producing strain can reduce its IMP-exporting ability, attempts were made to prepare vectors deficient in each of the genes.

The gene fragments for preparing the vectors were obtained by PCR using the genomic DNA of the ATCC6872 strain as a template.

Specifically, the PCR for impE1 was performed using primers of SEQ ID NOS: 5 and 6 and primers of SEQ ID NOS: 7 and 8; and the PCR for impE2 was performed using the primers of SEQ ID NOS: 9 and 10 and primers of SEQ ID NOS: 11 and 12 (Table 3).

TABLE 3

| SEQ ID NO | Primer | Sequence (5' to 3') |
|---|---|---|
| 5 | impE1 kop-1 | GCTCTAGACGAGAAAGCTAAAGCCGGTGA |
| 6 | impE1 kop-2 | GTTTTTAGCTACCATTGTTACACCCCGTGCAAGTTT |
| 7 | impE1 kop-3 | GCACGGGGTGTAACAATGGTAGCTAAAAACTCCACC |
| 8 | impE1 kop-4 | GCTCTAGAAATAGTTGGGGAAGTCCACTC |
| 9 | impE2 kop-1 | GCTCTAGACTTGGATGACCTGGTGGAAAA |
| 10 | impE2 kop-2 | CTTGGAGAAAATTTCCTACCATTCCAGTCCTTTCGT |
| 11 | impE2 kop-3 | GGACTGGAATGGTAGGAAATTTTCTCCAAGGGAAAT |
| 12 | impE2 kop-4 | GGACTAGTGGATTGTGTTGACGCACGATG |
| 13 | impE1E2kop-2 | CTTGGAGAAAATTTCTGTTACACCCCGTGCAAGTTT |
| 14 | impE1E2kop-3 | GCACGGGGTGTAACAGAAATTTTCTCCAAGGGAAAT |

In particular, the primers used were prepared based on information on a gene of *Corynebacterium stationis* (ATCC6872) (NCBI Genbank: NZ_CP014279) registered in NIH GenBank and the nucleotide sequences adjacent thereto.

PCR was performed by initial denaturation at 94° C. for 5 minutes; 25 cycles consisting of denaturation at 94° C. for 30 seconds, annealing at 52° C. for 30 minutes, and polymerization at 72° C. for 1 minute; and final polymerization at 72° C. for 5 minutes.

Overlapping PCR was performed using two fragments of the impE1 gene, which were amplified using the primers of SEQ ID NOS: 5 and 6 and the primers of SEQ ID NOS: 7 and 8, as templates, and as a result, a polynucleotide template (1.8 kbp) was obtained. The obtained gene fragment was cloned into a linearized pDZ vector (Korean Patent No. 10-0924065 and International Patent Publication No. 2008-033001), which was digested with the restriction enzyme (XbaI), and ligated using T4 ligase, and thereby the pDZ-ΔimpE1 vector was prepared. Additionally, overlapping polymerase chain reaction was performed using a fragment of the impE2 gene, amplified using the primers of SEQ ID NOS: 9 and 10, and two fragments of the impE2 gene, amplified using the primers of SEQ ID NOS: 11 and 12, as templates, and as a result, a polynucleotide template (1.7 kbp) was obtained. The obtained gene fragment was digested with restriction enzymes, XbaI and SpeI. The gene fragment was cloned using T4 ligase into a linearized pDZ vector, which had already been digested with the restriction enzyme (XbaI), and thereby the pDZ-4impE2 vector was prepared.

Example 2-3: Preparation of impE1- and impE2-Integration-Deficient Vectors

Since the impE1 and impE2 genes, which encode proteins involved in releasing the growth inhibition caused by IMP, are overlapped, there is a need to regulate both genes simultaneously. Therefore, attempts were made to prepare a vector in which both impE1 and impE2 are deficient.

For the PCR of impE1 and impE2 genes, primers of SEQ ID NOS: 5 and 13 and primers of SEQ ID NOS: 14 and 12 were used. The primers used were prepared based on information on a gene of *Corynebacterium stationis* (ATCC6872) (NCBI Genbank: NZ_CP014279) registered in NIH GenBank and the nucleotide sequences adjacent thereto. Overlapping PCR was performed using a fragment of the impE1 gene, amplified using the primers of SEQ ID NOS: 5 and 13, and two fragments of the impE2 gene, amplified using the primers of SEQ ID NOS: 14 and 12, as templates, and as a result, a polynucleotide template (2.0 kbp) was obtained. The obtained gene fragments were digested with XbaI and SpeI, respectively. The gene fragments were cloned using T4 ligase into a linearized pDZ vector, which had already been digested with the restriction enzyme (XbaI), and thereby the pDZ-ΔimpE1E2 vector was prepared.

Example 2-4: Preparation of impE1- and impE2-Deficient Strains

The two kinds of plasmids prepared in Example 2-2 and one kind of plasmid prepared in Example 2-3 were each transformed into the CJI0323 strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The genetic deficiency in the finally transformed strains was confirmed by performing PCR using the primer pairs of SEQ ID NOS: 5 and 8, SEQ ID NOS: 9 and 12, and SEQ ID NOS: 5 and 12.

The selected strains were named CJI0323_ΔimpE1, CJI0323_ΔimpE2, and CJI0323_ΔimpE1E2. Additionally, the abilities to produce IMP of these strains was evaluated.

The seed medium (2 mL) was dispensed into test tubes (diameter: 18 mm), which were then autoclaved, each inoculated with CJI0323, CJI0323_ΔimpE1, CJI0323_ΔimpE2, and CJI0323_ΔimpE1E2, shake-cultured at 30° C. for 24 hours, and used as seed culture solutions. The fermentation medium (29 mL) was dispensed into Erlenmeyer flasks (250 mL) for shaking and autoclaved at 121° C. for 15 minutes. Then, the seed culture solution (2 mL) was inoculated thereto and the resultant was cultured for 3 days. The culture conditions were set to 170 rpm, 30° C., and a pH of 7.5.

Upon completion of the culture, the amount of IMP produced was measured by HPLC, and the results of the culture are shown in Table 4 below.

TABLE 4

| Strain | IMP (g/L) |
|---|---|
| CJI0323 | 9.52 |
| CJI0323_ΔimpE1 | 1.92 |
| CJI0323_ΔimpE2 | 1.88 |
| CJI0323_ΔimpE1E2 | 1.80 |

The IMP amount accumulated in each strain was compared with that of the parent strain, *Corynebacterium stationis* CJI0323. As a result, it was found that, as shown in Table 4 above, the IMP concentrations of the strains CJI0323_ΔimpE1, CJI0323_ΔimpE2, and CJI0323_ΔimpE1E2 were reduced by about 8 g/L under the same conditions compared to the parent strain, confirming that ImpE1 and ImpE2 are proteins involved in the IMP export.

Example 3: Confirmation of Nucleotide Sequences of impE1 and impE2 of IMP-Producing Strain, CJI0323

In the case of the CJI0323 strain producing IMP at high concentration in Example 1, it is possible that the strain has an improved IMP-exporting ability so as to produce IMP at high concentration. Accordingly, an attempt was made to confirm the presence of any mutation in impE1 and impE2 of the CJI0323 strain.

The chromosomal DNA of the CJI0323 strain was amplified by polymerase chain reaction (hereinafter, "PCR"). Specifically, first, PCR was performed by repeating 28 cycles consisting of denaturation at 94° C. for 1 minute, annealing at 58° C. for 30 seconds, and polymerization at 72° C. for 2 minutes using the chromosomal DNA of the CJI0323 strain as a template along with the primers of SEQ ID NOS: 15 and 16 (Table 5), and thereby a fragment of about 2.8 kbp was amplified.

TABLE 5

| SEQ ID NO | Primer | Sequence (5' to 3') |
|---|---|---|
| 15 | impE1E2 seqF | GAACGGAGTCATCTCCTTTGC |
| 16 | impE1E2 seqR | CCAAACGCTCTGCAAGAAACTG |

Upon analysis of the nucleotide sequence using the same primers, it was confirmed that the 490$^{th}$ nucleotide of the impE1 gene (i.e., g) was substituted with 'a', compared to the nucleotide sequence of the wild-type strain, ATCC6872. This substitution indicates that there was a modification in which the 164$^{th}$ amino acid of the ImpE1 protein (i.e., glutamic acid) was substituted with lysine.

Additionally, it was confirmed that the 4$^{th}$ nucleotide of the impE2 gene (i.e., g) was substituted with 'a' (this means that the 666$^{th}$ nucleotide of the impE1 gene (i.e., g) was substituted with 'a') and the 191$^{st}$ nucleotide of the impE1 gene (i.e., g) was substituted with 'a'. These substitutions indicate that there were modifications in which the 2nd amino acid of the ImpE2 protein (i.e., valine), which corresponds to the 222$^{nd}$ amino acid of the ImpE1 protein, was substituted with isoleucine; and the 64$^{th}$ amino acid of the ImpE2 protein (i.e., glycine) was substituted with glutamic acid.

The impE1 nucleotide of the CJI0323 strain was named impE1_CJI0323 (SEQ ID NO: 143) and the protein thereof was named ImpE1_CJI0323 (SEQ ID NO: 141), whereas the impE2 nucleotide of the CJI0323 strain was named impE2_CJI0323 (SEQ ID NO: 144) and the protein thereof was named ImpE2_CJI0323 (SEQ ID NO: 142).

Example 4: Recovery of Modifications in impE1 and impE2

Example 4-1: Preparation of Vectors for Recovering Modifications in impE1 or impE2

In Example 3, the presence of any modification in impE1 and impE2 of the IMP-producing strain CJI0323 was examined. As a result, it was confirmed that impE1 had one modification and impE2 had two modifications. Since the CJI0323 strain produces IMP at a high concentration, it is highly likely that the modification is one that can improve the ability to export IMP. Accordingly, after recovering the mutated impE1 and impE2 to the native wild-type ImpE without modification, the following experiment was performed to confirm whether each modification actually imparted the IMP-exporting ability.

To prepare a recovery vector, PCR was performed using Corynebacterium stationis ATCC6872 as a template.

The impE1 impE2 gene fragment amplified using the primers of SEQ ID NOS: 17 and 18 was treated with a restriction enzyme, XbaI, and cloned into the XbaI restriction site on the pDZ vector, and thereby the pDZ-impE1E2 (WT) was prepared.

Example 4-2: Preparation of Vectors with Single Modification in impE1 or impE2

A vector with a single E164K modification in the ImpE1 gene was prepared using the native wild-type strain, Corynebacterium stationis ATCC6872, as a template along with the primers of SEQ ID NOS: 19 and 20 and primers of SEQ ID NOS: 21 and 22. Overlapping PCR was performed using an E164K-1 gene fragment amplified using the primers of SEQ ID NOS: 19 and 20 and two E164K-2 gene fragments amplified using the primers of SEQ ID NOS: 21 and 22, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE1(E164K) vector was prepared.

A vector with a single V2I modification in the ImpE2 gene was prepared using the ATCC6872 strain as a template along with the primers of SEQ ID NOS: 19 and 23 and primers of SEQ ID NOS: 24 and 22. Overlapping PCR was performed using a V2I-1 gene fragment amplified using the primers of SEQ ID NOS: 19 and 23 and two V2I-2 gene fragments amplified using the primers of SEQ ID NOS: 24 and 22, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE2(V2I) vector was prepared.

A vector with a single G64E modification in the ImpE2 gene was prepared using the ATCC6872 strain as a template along with the primers of SEQ ID NOS: 19 and 25 and primers of SEQ ID NOS: 26 and 22. Overlapping PCR was performed using a G64E-1 gene fragment amplified using the primers of SEQ ID NOS: 19 and 25 and two G64E-2 gene fragments amplified using the primers of SEQ ID NOS: 26 and 22, and thereby a template with a 1.8 kbp polynucleotide was obtained. The obtained gene fragments were digested with XbaI and cloned into a linearized pDZ vector, which had already been digested with XbaI, using T4 ligase, and thereby the pDZ-impE2(G64E) vector was prepared.

TABLE 6

| SEQ ID NO | Primer | Sequence (5' to 3') |
|---|---|---|
| 17 | impE1E2 WT F | GCTCTAGAGAACGGAGTCATCTCCTTTGC |
| 18 | impE1E2 WT R | GCTCTAGACCAAACGCTCTGCAAGAAACTG |
| 19 | impE1 164K-1 | GCTCTAGACTTGGATGACCTGGTGGAAAA |
| 20 | impE1 164K-2 | CTGGGGCGCGTTGTTTTTCAGGATGCTCCCGAAGACG |
| 21 | impE1 164K-3 | AACAACGCGCCCCAGAATTGG |
| 22 | impE1 164K-4 | GCTCTAGAAATAGTTGGGGAAGTCCACTC |
| 23 | impE2 V2I-2 | TGGAGTTTTTAGCTATCATTCCAGTCCTTTCGTGTAA |
| 24 | impE2 V2I-3 | TAGCTAAAAACTCCACCCCAA |

TABLE 6-continued

| SEQ ID NO | Primer | Sequence (5' to 3') |
|---|---|---|
| 25 | impE2 G64E-2 | CCGAAAATCATCTGCTCCAAAGAGCTCATCAGCATGG |
| 26 | impE2 G64E-3 | GCAGATGATTTTCGGTTCCGC |

Example 4-3: Recovery of impE1, impE2 Modifications and Preparation of Strains with Single Modification The plasmid prepared in Example 4-1 was transformed into the CJI0323 strain by electroporation (using the transformation method disclosed in *Appl. Microbiol. Biotechnol.* (1999) 52: 541 to 545). The strains in which the vector was inserted into the chromosome by recombination of the homologous sequences were selected on a medium containing kanamycin (25 mg/L). The selected primary strains were subjected to a second cross-over. The recovery of the modification in the finally transformed strains was confirmed by performing PCR using the primer pair of SEQ ID NOS: 15 and 16, followed by nucleotide sequencing analysis. The prepared strain was named CJI0323_impE1E2 (WT).

The three kinds of plasmids prepared in Example 4-2 were each transformed into the CJI0323_impE1E2(WT) strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The selected strains were named CJI0323_impE1(E164K), CJI0323_impE2(V2I), and CJI0323_impE2(G64E).

The *Corynebacterium stationis* CJI0323_impE1(E164K), *Corynebacterium stationis* CJI0323_impE2(V2I), and *Corynebacterium stationis* CJI0323_impE2(G64E) strains were deposited under the Budapest Treaty to the Korean Culture Center of Microorganisms (KCCM) on Nov. 2, 2018. In addition, the strains were designated with Accession Nos. KCCM12359P, KCCM12360P, and KCCM12361P, respectively.

Example 4-4: Preparation of impE1- and impE2-Integration-Modified Strains

The pDZ-impE2(V2I) and pDZ-impE2(G64E) plasmids prepared in Example 4-2 were transformed into the CJI0323_impE1(E164K) strain by electroporation (using the transformation method disclosed in Appl. Microbiol. Biotechnol. (1999) 52: 541 to 545). The strains in which the vectors were inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The prepared strains were named CJI0323_impE1(E164K)_impE2(V2I) and CJI0323_impE1 (164K)_impE2(G64E).

The pDZ-impE2(G64E) plasmid was transformed into the CJI0323_impE2(V2I) strain by electroporation (using the transformation method disclosed in Appl. Microbiol. Biotechnol. (1999) 52: 541 to 545). The strains in which the vector was inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The selected strain was named CJI0323_impE2 (V2I)(G64E).

Example 4-5: Evaluation of Strains with impE1, impE2 Modifications

The seed medium (2 mL) was dispensed into test tubes (diameter: 18 mm), which were then autoclaved, each inoculated with CJI0323_impE1E2(W7), CJI0323_impE1 (E164K), CJI0323_impE2(V2I), CJI0323_impE2(G64E), CJI0323_impE1(E164K)_impE2(V2I), CJI0323_impE1 (E164K)_impE2(G64E), and CJI0323_impE2(V2I)(G64E), shake-cultured at 30° C. for 24 hours, and used as seed culture solutions. The fermentation medium (29 mL) was dispensed into Erlenmeyer flasks (250 mL) for shaking and autoclaved at 121° C. for 15 minutes. Then, the seed culture solutions (2 mL) were inoculated thereto and the resultants were cultured for 3 days. The culture conditions were set to 170 rpm, 30° C., and a pH of 7.5.

Upon completion of the culture, the amount of IMP produced was measured by HPLC, and the results of the culture are shown in Table 7 below.

TABLE 7

| Strain | IMP (g/L) |
|---|---|
| CJI0323 | 9.52 |
| CJI0323_impE1E2(WT) | 2.32 |
| CJI0323_impE1(E164K) | 2.57 |
| CJI0323_impE2(V2I) | 3.11 |
| CJI0323_impE2(G64E) | 3.27 |
| CJI0323_impE1(E164K)_impE2(V2I) | 4.24 |
| CJI0323_impE1(E164K)_impE2(G64E) | 6.27 |
| CJI0323_impE2(V2I)(G64E) | 7.35 |

As shown above, it was confirmed that with respect to each modification position, one kind of modification, the integration of two kinds of modifications, and the integration of three kinds of modifications were all involved in the IMP export. Accordingly, in a microorganism of the genus *Corynebacterium* which does not produce IMP or produces only a small amount thereof, the increase in the amount of IMP production due to modifications of the ImpE protein of the present disclosure can be interpreted to be very meaningful.

Example 5: Substitution of Amino Acids in impE1, impE2 Modifications with Another Amino Acids

Example 5-1: Preparation of Vectors for Substitutional Insertion of Amino Acids in impE1, impE2 Modifications To confirm the positional importance of the representative three kinds of modifications (i.e., impE1(E164K), impE2 (V2I), and impE2(G64E)) with enhanced abilities to produce IMP as identified in the results above, a vector for introducing modifications (e.g., a modification of substituting the 164$^{th}$ amino acid in the amino acid sequence of impE1, the 2$^{nd}$ amino acid in the amino acid sequence of impE2, and the 64$^{th}$ amino acid in the amino acid sequence of impE2 with an another amino acid) was prepared.

Firstly, the procedure of preparing the vector for the introduction of the ImpE1(E164K) modification is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 27 and each of SEQ ID NOS: 28 to 45. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained. Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 46 and each of SEQ ID NOS: 47 to 64. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained.

Overlapping PCR was performed using two fragments obtained from the above results as a template, and thereby 18 kinds of 1.4 kbp polynucleotides to be used as templates were obtained. The obtained gene fragments were digested with a restriction enzyme, SpeI, ligated to the linearized pDZ vector, which had already been digested with a restriction enzyme, XbaI, transformed into *E. coli* DH5a, and the transformants were plated on a solid LB medium containing kanamycin (25 mg/L).

The sequence information on the primers used for the preparation of the vector is shown in Table 8 below.

TABLE 8

| SEQ ID NO | Primer | Sequence (5' to 3') |
|---|---|---|
| 27 | SpeI-impE1 164 1F | GGGACTAGTGATTCCGGCCAACTGTCG |
| 28 | impE1 164-R 1R | TGGGGCGCGTTGGCGTTCAGGATGCTC |
| 29 | impE1 164-H 1R | TGGGGCGCGTTGGTGTTCAGGATGCTC |
| 30 | impE1 164-D 1R | TGGGGCGCGTTGATCTTCAGGATGCTC |
| 31 | impE1 164-S 1R | TGGGGCGCGTTGGGATTCAGGATGCTC |
| 32 | impE1 164-T 1R | TGGGGCGCGTTGGGTTTCAGGATGCTC |
| 33 | impE1 164-N 1R | TGGGGCGCGTTGGTTTTCAGGATGCTC |
| 34 | impE1 164-Q 1R | TGGGGCGCGTTGCTGTTCAGGATGCTC |
| 35 | impE1 164-C 1R | TGGGGCGCGTTGGCATTCAGGATGCTC |
| 36 | impE1 164-G 1R | TGGGGCGCGTTGGCCTTCAGGATGCTC |
| 37 | impE1 164-P 1R | TGGGGCGCGTTGCGGTTCAGGATGCTC |
| 38 | impE1 164-A 1R | TGGGGCGCGTTGGGCTTCAGGATGCTC |
| 39 | impE1 164-V 1R | TGGGGCGCGTTGGACTTCAGGATGCTC |
| 40 | impE1 164-I 1R | TGGGGCGCGTTGGATTTCAGGATGCTC |
| 41 | impE1 164-L 1R | TGGGGCGCGTTGCAGTTCAGGATGCTC |
| 42 | impE1 164-M 1R | TGGGGCGCGTTGCATTTCAGGATGCTC |
| 43 | impE1 164-F 1R | TGGGGCGCGTTGGAATTCAGGATGCTC |
| 44 | impE1 164-Y 1R | TGGGGCGCGTTGGTATTCAGGATGCTC |
| 45 | impE1 164-W 1R | TGGGGCGCGTTGCCATTCAGGATGCTC |
| 46 | SpeI-impE1 164 2R | GGGACTAGTCATGAACTTGCCGCGCTC |
| 47 | impE1 164-R 2F | GAGCATCCTGAACGCCAACGCGCCCCA |
| 48 | impE1 164-H 2F | GAGCATCCTGAACACCAACGCGCCCCA |
| 49 | impE1 164-D 2F | GAGCATCCTGAAGATCAACGCGCCCCA |

TABLE 8-continued

| SEQ ID NO | Primer | Sequence (5' to 3') |
|---|---|---|
| 50 | impE1 164-S 2F | GAGCATCCTGAATCCCAACGCGCCCCA |
| 51 | impE1 164-T 2F | GAGCATCCTGAAACCCAACGCGCCCCA |
| 52 | impE1 164-N 2F | GAGCATCCTGAAAACCAACGCGCCCCA |
| 53 | impE1 164-Q 2F | GAGCATCCTGAACAGCAACGCGCCCCA |
| 54 | impE1 164-C 2F | GAGCATCCTGAATGCCAACGCGCCCCA |
| 55 | impE1 164-G 2F | GAGCATCCTGAAGGCCAACGCGCCCCA |
| 56 | impE1 164-P 2F | GAGCATCCTGAACCGCAACGCGCCCCA |
| 57 | impE1 164-A 2F | GAGCATCCTGAAGCCCAACGCGCCCCA |
| 58 | impE1 164-V 2F | GAGCATCCTGAAGTCCAACGCGCCCCA |
| 59 | impE1 164-I 2F | GAGCATCCTGAAATCCAACGCGCCCCA |
| 60 | impE1 164-L 2F | GAGCATCCTGAACTGCAACGCGCCCCA |
| 61 | impE1 164-M 2F | GAGCATCCTGAAATGCAACGCGCCCCA |
| 62 | impE1 164-F 2F | GAGCATCCTGAATTCCAACGCGCCCCA |
| 63 | impE1 164-Y 2F | GAGCATCCTGAATACCAACGCGCCCCA |
| 64 | impE1 164-W 2F | GAGCATCCTGAATGGCAACGCGCCCCA |

After selecting by PCR the colonies transformed with the vector into which the target gene was inserted, the plasmids were obtained using a conventionally known plasmid extraction method. The information on the obtained plasmids is shown in Table 9 below.

TABLE 9

| No. | Plasmid |
|---|---|
| 1 | pDZ-impE1 164R |
| 2 | pDZ-impE1 164H |
| 3 | pDZ-impE1 164D |
| 4 | pDZ-impE1 164S |
| 5 | pDZ-impE1 164T |
| 6 | pDZ-impE1 164N |
| 7 | pDZ-impE1 164Q |
| 8 | pDZ-impE1 164C |
| 9 | pDZ-impE1 164G |
| 10 | pDZ-impE1 164P |
| 11 | pDZ-impE1 164A |
| 12 | pDZ-impE1 164V |
| 13 | pDZ-impE1 164I |
| 14 | pDZ-impE1 164L |
| 15 | pDZ-impE1 164M |
| 16 | pDZ-impE1 164F |
| 17 | pDZ-impE1 164Y |
| 18 | pDZ-impE1 164W |

Secondly, the procedure of preparing the vector for the introduction of the ImpE2(V2I) is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 65 and each of SEQ ID NOS: 66 to 83. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained. Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 84 and each of SEQ ID NOS: 85 to 102. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 0.7 kbp polynucleotides were obtained.

Overlapping PCR was performed using two fragments obtained from the above results as a template, and thereby 18 kinds of 1.4 kbp polynucleotides to be used as templates were obtained. The obtained gene fragments were digested with a restriction enzyme, XbaI, ligated to the linearized pDZ vector, which had already been digested with a restriction enzyme, XbaI, transformed into *E. coli* DH5a, and the transformants were plated on a solid LB medium containing kanamycin (25 mg/L).

The sequence information on the primers used for the preparation of the vector is shown in Table 10 below.

TABLE 10

| SEQ ID NO | Primer | Sequence (5' to 3') |
|---|---|---|
| 65 | XbaI-impE2 2 1F | GGGTCTAGATTGCATGCTGTGCAAGA |
| 66 | impE2 2-R 1R | GGAGTTTTTAGCGCGCATTCCAGTCCT |

TABLE 10-continued

| SEQ ID NO | Primer | Sequence (5' to 3') |
|---|---|---|
| 67 | impE2 2-H 1R | GGAGTTTTTAGCGTGCATTCCAGTCCT |
| 68 | impE2 2-K 1R | GGAGTTTTTAGCCTTCATTCCAGTCCT |
| 69 | impE2 2-D 1R | GGAGTTTTTAGCGTCCATTCCAGTCCT |
| 70 | impE2 2-E 1R | GGAGTTTTTAGCTTCCATTCCAGTCCT |
| 71 | impE2 2-S 1R | GGAGTTTTTAGCGGACATTCCAGTCCT |
| 72 | impE2 2-T 1R | GGAGTTTTTAGCGGTCATTCCAGTCCT |
| 73 | impE2 2-N 1R | GGAGTTTTTAGCGTTCATTCCAGTCCT |
| 74 | impE2 2-Q 1R | GGAGTTTTTAGCCTGCATTCCAGTCCT |
| 75 | impE2 2-C 1R | GGAGTTTTTAGCGCACATTCCAGTCCT |
| 76 | impE2 2-G 1R | GGAGTTTTTAGCGCCCATTCCAGTCCT |
| 77 | impE2 2-P 1R | GGAGTTTTTAGCTGGCATTCCAGTCCT |
| 78 | impE2 2-A 1R | GGAGTTTTTAGCAGCCATTCCAGTCCT |
| 79 | impE2 2-L 1R | GGAGTTTTTAGCCAGCATTCCAGTCCT |
| 80 | impE2 2-M 1R | GGAGTTTTTAGCCATCATTCCAGTCCT |
| 81 | impE2 2-F 1R | GGAGTTTTTAGCGAACATTCCAGTCCT |
| 82 | impE2 2-Y 1R | GGAGTTTTTAGCGTACATTCCAGTCCT |
| 83 | impE2 2-W 1R | GGAGTTTTTAGCCCACATTCCAGTCCT |
| 84 | XbaI-impE2 2 2R | GGGTCTAGATTGCTCGCCCACGCGCA |
| 85 | impE2 2-R 2F | AGGACTGGAATGCGCGCTAAAAACTCC |
| 86 | impE2 2-H 2F | AGGACTGGAATGCACGCTAAAAACTCC |
| 87 | impE2 2-K 2F | AGGACTGGAATGAAGGCTAAAAACTCC |
| 88 | impE2 2-D 2F | AGGACTGGAATGGACGCTAAAAACTCC |
| 89 | impE2 2-E 2F | AGGACTGGAATGGAAGCTAAAAACTCC |
| 90 | impE2 2-S 2F | AGGACTGGAATGTCCGCTAAAAACTCC |
| 91 | impE2 2-T 2F | AGGACTGGAATGACCGCTAAAAACTCC |
| 92 | impE2 2-N 2F | AGGACTGGAATGAACGCTAAAAACTCC |
| 93 | impE2 2-Q 2F | AGGACTGGAATGCAGGCTAAAAACTCC |
| 94 | impE2 2-C 2F | AGGACTGGAATGTGCGCTAAAAACTCC |
| 95 | impE2 2-G 2F | AGGACTGGAATGGGCGCTAAAAACTCC |
| 96 | impE2 2-P 2F | AGGACTGGAATGCCAGCTAAAAACTCC |
| 97 | impE2 2-A 2F | AGGACTGGAATGGCTGCTAAAAACTCC |
| 98 | impE2 2-L 2F | AGGACTGGAATGCTGGCTAAAAACTCC |
| 99 | impE2 2-M 2F | AGGACTGGAATGATGGCTAAAAACTCC |
| 100 | impE2 2-F 2F | AGGACTGGAATGTTCGCTAAAAACTCC |
| 101 | impE2 2-Y 2F | AGGACTGGAATGTACGCTAAAAACTCC |
| 102 | impE2 2-W 2F | AGGACTGGAATGTGGGCTAAAAACTCC |

After selecting by PCR the colonies transformed with the vector into which the target gene was inserted, the plasmids were obtained using a conventionally known plasmid extraction method. The information on the obtained plasmids is shown in Table 11 below.

TABLE 11

| No. | Plasmid |
|---|---|
| 1 | pDZ-impE2 2R |
| 2 | pDZ-impE2 2H |
| 3 | pDZ-impE2 2K |
| 4 | pDZ-impE2 2D |
| 5 | pDZ-impE2 2E |
| 6 | pDZ-impE2 2S |
| 7 | pDZ-impE2 2T |
| 8 | pDZ-impE2 2N |
| 9 | pDZ-impE2 2Q |
| 10 | pDZ-impE2 2C |
| 11 | pDZ-impE2 2G |
| 12 | pDZ-impE2 2P |
| 13 | pDZ-impE2 2A |
| 14 | pDZ-impE2 2L |
| 15 | pDZ-impE2 2M |
| 16 | pDZ-impE2 2F |
| 17 | pDZ-impE2 2Y |
| 18 | pDZ-impE2 2W |

Lastly, the procedure of preparing the vector for the introduction of the ImpE2(G64E) is as follows.

Based on the reported polynucleotide sequences, the chromosomal genes of *Corynebacterium stationis* CJI0323 were isolated, and gene fragments were obtained by performing PCR using the chromosomal DNA of *Corynebacterium stationis* CJI0323 as a template denaturation at 94° C. for 30 seconds, annealing at 55° C. for 30 seconds, and poly along with primer pairs between the primer of SEQ ID NO: 103 and each of SEQ ID NOS: 104 to 121. PCR was performed by initial denaturation at 94° C. for 5 minutes; 20 cycles consisting of denaturation at 94° C. for 30 seconds, annealing at 55° C. for 30 seconds, and polymerization at 72° C. for 1 minute; and final polymerization at 72° C. for 5 minutes. As a result, 18 kinds of 1 kbp polynucleotides were obtained. Then, the chromosomal genes of *Corynebacterium stationis* CJI0323 were isolated, and gene fragments were obtained by performing PCR using the chromosomal DNA of *Corynebacterium stationis* CJI0323 as a template along with primer pairs between the primer of SEQ ID NO: 84 and each of SEQ ID NOS: 85 to 102. PCR was performed by initial denaturation at 94° C. for 5 minutes; 20 cycles consisting of polymerization at 72° C. for 1 minute; and final polymerization at 72° C. for 5 minutes. As a result, 18 kinds of 1 kbp polynucleotides were obtained.

Overlapping PCR was performed using two fragments obtained from the above results as a template, and thereby 18 kinds of 2 kbp polynucleotides to be used as templates were obtained. The obtained gene fragments were digested with a restriction enzyme, XbaI, ligated to the linearized pDZ vector, which had already been digested with a restriction enzyme, XbaI, transformed into *E. coli* DH5α, and the transformants were plated on a solid LB medium containing kanamycin (25 mg/L).

The sequence information on the primers used for the preparation of the vector is shown in Table 12 below.

TABLE 12

| SEQ ID NO | Primer | Sequence (5' to 3') |
|---|---|---|
| 103 | XbaI-impE2 64 1F | GGGTCTAGAAAAGAGCTTAAGGCAGCTGCT |
| 104 | impE2 64-R 1R | GAAAATCATCTGGCGCAAAGAGCTCAT |
| 105 | impE2 64-H 1R | GAAAATCATCTGGTGCAAAGAGCTCAT |
| 106 | impE2 64-D 1R | GAAAATCATCTGGTCCAAAGAGCTCAT |
| 107 | impE2 64-K 1R | GAAAATCATCTGCTTCAAAGAGCTCAT |
| 108 | impE2 64-S 1R | GAAAATCATCTGGGACAAAGAGCTCAT |
| 109 | impE2 64-T 1R | GAAAATCATCTGGGTCAAAGAGCTCAT |
| 110 | impE2 64-N 1R | GAAAATCATCTGGTTCAAAGAGCTCAT |
| 111 | impE2 64-Q 1R | GAAAATCATCTGCTGCAAAGAGCTCAT |
| 112 | impE2 64-C 1R | GAAAATCATCTGGCACAAAGAGCTCAT |
| 113 | impE2 64-P 1R | GAAAATCATCTGTGGCAAAGAGCTCAT |
| 114 | impE2 64-A 1R | GAAAATCATCTGAGCCAAAGAGCTCAT |
| 115 | impE2 64-V 1R | GAAAATCATCTGGACCAAAGAGCTCAT |
| 116 | impE2 64-I 1R | GAAAATCATCTGGATCAAAGAGCTCAT |
| 117 | impE2 64-L 1R | GAAAATCATCTGCAGCAAAGAGCTCAT |
| 118 | impE2 64-M 1R | GAAAATCATCTGCATCAAAGAGCTCAT |
| 119 | impE2 64-F 1R | GAAAATCATCTGGAACAAAGAGCTCAT |
| 120 | impE2 64-Y 1R | GAAAATCATCTGGTACAAAGAGCTCAT |
| 121 | impE2 64-W 1R | GAAAATCATCTGCCACAAAGAGCTCAT |
| 122 | XbaI-impE2 64 2R | GGGTCTAGACGGTCAATGAAGTCTCAACGG |

TABLE 12-continued

| SEQ ID NO | Primer | Sequence (5' to 3') |
|---|---|---|
| 123 | impE2 64-R 2F | ATGAGCTCTTTGCGCCAGATGATTTTC |
| 124 | impE2 64-H 2F | ATGAGCTCTTTGCACCAGATGATTTTC |
| 125 | impE2 64-D 2F | ATGAGCTCTTTGGACCAGATGATTTTC |
| 126 | impE2 64-K 2F | ATGAGCTCTTTGAAGCAGATGATTTTC |
| 127 | impE2 64-S 2F | ATGAGCTCTTTGTCCCAGATGATTTTC |
| 128 | impE2 64-T 2F | ATGAGCTCTTTGACCCAGATGATTTTC |
| 129 | impE2 64-N 2F | ATGAGCTCTTTGAACCAGATGATTTTC |
| 130 | impE2 64-Q 2F | ATGAGCTCTTTGCAGCAGATGATTTTC |
| 131 | impE2 64-C 2F | ATGAGCTCTTTGTGCCAGATGATTTTC |
| 132 | impE2 64-P 2F | ATGAGCTCTTTGCCACAGATGATTTTC |
| 133 | impE2 64-A 2F | ATGAGCTCTTTGGCTCAGATGATTTTC |
| 134 | impE2 64-V 2F | ATGAGCTCTTTGGTCCAGATGATTTTC |
| 135 | impE2 64-I 2F | ATGAGCTCTTTGATCCAGATGATTTTC |
| 136 | impE2 64-L 2F | ATGAGCTCTTTGCTGCAGATGATTTTC |
| 137 | impE2 64-M 2F | ATGAGCTCTTTGATGCAGATGATTTTC |
| 138 | impE2 64-F 2F | ATGAGCTCTTTGTTCCAGATGATTTTC |
| 139 | impE2 64-Y 2F | ATGAGCTCTTTGTACCAGATGATTTTC |
| 140 | impE2 64-W 2F | ATGAGCTCTTTGTGGCAGATGATTTTC |

After selecting by PCR the colonies transformed with the vector into which the target gene was inserted, the plasmids were obtained using a conventionally known plasmid extraction method. The information on the obtained plasmids is shown in Table 13 below.

TABLE 13

| No. | Plasmid |
|---|---|
| 1 | pDZ-impE2 64R |
| 2 | pDZ-impE2 64H |
| 3 | pDZ-impE2 64D |
| 4 | pDZ-impE2 64K |
| 5 | pDZ-impE2 64S |
| 6 | pDZ-impE2 64T |
| 7 | pDZ-impE2 64N |
| 8 | pDZ-impE2 64Q |
| 9 | pDZ-impE2 64C |
| 10 | pDZ-impE2 64P |
| 11 | pDZ-impE2 64A |
| 12 | pDZ-impE2 64V |
| 13 | pDZ-impE2 64I |
| 14 | pDZ-impE2 64L |
| 15 | pDZ-impE2 64M |
| 16 | pDZ-impE2 64F |
| 17 | pDZ-impE2 64Y |
| 18 | pDZ-impE2 64W |

Example 5-2: Preparation of Strains where Amino Acids at Positions of Modified Products (ImpE1, ImpE2) are Substituted with Another Amino Acids, and Comparison of Ability to Produce IMP The 54 kinds of plasmids prepared in Example 5-1 were transformed into the CJI0323 strain. The strains in which the vector was inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis. The strain names according to the inserted modifications are shown in Table 14 below.

TABLE 14

| No. | Strain |
|---|---|
| 1 | CJI0323::impE1(E164R) |
| 2 | CJI0323::impE1(E164H) |
| 3 | CJI0323::impE1(E164D) |
| 4 | CJI0323::impE1(E164S) |
| 5 | CJI0323::impE1(E164T) |
| 6 | CJI0323::impE1(E164N) |
| 7 | CJI0323::impE1(E164Q) |
| 8 | CJI0323::impE1(E164C) |
| 9 | CJI0323::impE1(E164G) |
| 10 | CJI0323::impE1(E164P) |
| 11 | CJI0323::impE1(E164A) |
| 12 | CJI0323::impE1(E164V) |
| 13 | CJI0323::impE1(E164I) |
| 14 | CJI0323::impE1(E164L) |
| 15 | CJI0323::impE1(E164M) |
| 16 | CJI0323::impE1(E164F) |
| 17 | CJI0323::impE1(E164Y) |
| 18 | CJI0323::impE1(E164W) |
| 19 | CJI0323::impE2(V2R) |
| 20 | CJI0323::impE2(V2H) |
| 21 | CJI0323::impE2(V2K) |
| 22 | CJI0323::impE2(V2D) |

TABLE 14-continued

| No. | Strain |
|---|---|
| 23 | CJI0323::impE2(V2E) |
| 24 | CJI0323::impE2(V2S) |
| 25 | CJI0323::impE2(V2T) |
| 26 | CJI0323::impE2(V2N) |
| 27 | CJI0323::impE2(V2Q) |
| 28 | CJI0323::impE2(V2C) |
| 29 | CJI0323::impE2(V2G) |
| 30 | CJI0323::impE2(V2P) |
| 31 | CJI0323::impE2(V2A) |
| 32 | CJI0323::impE2(V2L) |
| 33 | CJI0323::impE2(V2M) |
| 34 | CJI0323::impE2(V2F) |
| 35 | CJI0323::impE2(V2Y) |
| 36 | CJI0323::impE2(V2W) |
| 37 | CJI0323::impE2(G64R) |
| 38 | CJI0323::impE2(G64H) |
| 39 | CJI0323:impE2(G64D) |
| 40 | CJI0323::impE2(G64K) |
| 41 | CJI0323::impE2(G64S) |
| 42 | CJI0323::impE2(G64T) |
| 43 | CJI0323::impE2(G64N) |
| 44 | CJI0323::impE2(G64Q) |
| 45 | CJI0323::impE2(G64C) |
| 46 | CJI0323::impE2(G64P) |
| 47 | CJI0323::impE2(G64A) |
| 48 | CJI0323::impE2(G64V) |
| 49 | CJI0323::impE2(G64I) |
| 50 | CJI0323:impE2(G64L) |
| 51 | CJI0323::impE2(G64M) |
| 52 | CJI0323::impE2(G64F) |
| 53 | CJI0323:impE2(G64Y) |
| 54 | CJI0323::impE2(G64W) |

The cultivation was performed in the same manner as in Example 1 and the concentration of IMP produced thereof was analyzed (Table 15).

TABLE 15

Concentration (g/L) of IMP production in strains with combined introduction of impE1, impE2 modifications

|  | Strain | Average IMP |
|---|---|---|
| Control | CJI0323_impE1E2(WT) | 2.32 |
| 1 | CJI0323::impE1(E164R) | 9.42 |
| 2 | CJI0323::impE1(E164H) | 8.47 |
| 3 | CJI0323::impE1(E164D) | 7.37 |
| 4 | CJI0323::impE1(E164S) | 8.56 |
| 5 | CJI0323::impE1(E164T) | 8.85 |
| 6 | CJI0323::impE1(E164N) | 9.13 |
| 7 | CJI0323::impE1(E164Q) | 7.45 |
| 8 | CJI0323::impE1(E164C) | 7.37 |
| 9 | CJI0323::impE1(E164G) | 9.13 |
| 10 | CJI0323::impE1(E164P) | 9.43 |
| 11 | CJI0323::impE1(E164A) | 7.44 |
| 12 | CJI0323::impE1(E164V) | 8.18 |
| 13 | CJI0323::impE1(E164I) | 8.09 |
| 14 | CJI0323::impE1(E164L) | 7.85 |
| 15 | CJI0323::impE1(E164M) | 7.39 |
| 16 | CJI0323::impE1(E164F) | 7.56 |
| 17 | CJI0323::impE1(E164Y) | 7.60 |
| 18 | CJI0323::impE1(E164W) | 8.56 |
| 19 | CJI0323::impE2(V2R) | 7.99 |
| 20 | CJI0323::impE2(V2H) | 8.75 |
| 21 | CJI0323::impE2(V2K) | 8.66 |
| 22 | CJI0323::impE2(V2D) | 8.28 |
| 23 | CJI0323::impE2(V2E) | 9.32 |
| 24 | CJI0323::impE2(V2S) | 6.37 |
| 25 | CJI0323::impE2(V2T) | 8.37 |
| 26 | CJI0323::impE2(V2N) | 9.80 |
| 27 | CJI0323::impE2(V2Q) | 7.04 |
| 28 | CJI0323::impE2(V2C) | 7.23 |
| 29 | CJI0323::impE2(V2G) | 7.71 |
| 30 | CJI0323::impE2(V2P) | 7.80 |
| 31 | CJI0323::impE2(V2A) | 6.57 |
| 32 | CJI0323::impE2(V2L) | 6.42 |
| 33 | CJI0323::impE2(V2M) | 9.20 |
| 34 | CJI0323::impE2(V2F) | 9.43 |
| 35 | CJI0323::impE2(V2Y) | 8.37 |
| 36 | CJI0323::impE2(V2W) | 7.22 |
| 37 | CJI0323::impE2(G64R) | 4.42 |
| 38 | CJI0323::impE2(G64H) | 5.14 |
| 39 | CJI0323::impE2(G64D) | 11.53 |
| 40 | CJI0323::impE2(G64K) | 4.8 |
| 41 | CJI0323::impE2(G64S) | 5.7 |
| 42 | CJI0323::impE2(G64T) | 5.52 |
| 43 | CJI0323::impE2(G64N) | 5.9 |
| 44 | CJI0323::impE2(G64Q) | 4.8 |
| 45 | CJI0323::impE2(G64C) | 5.9 |
| 46 | CJI0323::impE2(G64P) | 4.75 |
| 47 | CJI0323::impE2(G64A) | 4.58 |
| 48 | CJI0323::impE2(G64V) | 4.56 |
| 49 | CJI0323::impE2(G64I) | 5.89 |
| 50 | CJI0323::impE2(G64L) | 5.6 |
| 51 | CJI0323::impE2(G64M) | 4.3 |
| 52 | CJI0323::impE2(G64F) | 5.89 |
| 53 | CJI0323::impE2(G64Y) | 4.6 |
| 54 | CJI0323::impE2(G64W) | 4.76 |

As shown above, all of the modified strains showed an increase in the ability to produce IMP compared to each of the control strains, and thus, it was confirmed that the three positions of modification are important sites that have a significant effect on the increase of the ability of the ImpE protein with respect to IMP export.

Example 6: Introduction of impE1, impE2 Modifications Based on IMP-Producing Strains Example 6-1: Preparation of Strains with impE1, impE2 Modifications Based on IMP-Producing Strains To confirm the effect of introduction of impE1 and impE2 modifications, An IMP-producing strain was prepared in which the activities of adenylosuccinate synthetase and IMP dehydrogenase corresponding to the degradation pathway of IMP in the ATCC6872 strain were attenuated. The initiation codon was changed by changing the first base from 'a' to 't' in each nucleotide sequence of the two genes purA and guaB, which encode the two enzymes.

The strain in which the expression of the two genes was attenuated in the ATCC6872 strain was named CJI9088. The pDZ-impE1(E164K), pDZ-impE2(V2I), and pDZ-impE2 (G64E) vectors prepared in Example 4-2 were transformed into the CJI9088 strain by electroporation, and the pDZ-impE2(G64D) vector prepared in Example 5-1 was transformed into the CJI9088_impE1(E164K)_impE2(V2I) strain by electroporation. The strains in which the vectors were inserted into the chromosome by recombination of the homologous sequences were selected on a medium containing kanamycin (25 mg/L). The selected primary strains were subjected to a second cross-over. The introduction of the modification in the finally transformed strains was confirmed by performing PCR using the primer pair of SEQ ID NOS: 15 and 16, followed by nucleotide sequencing analysis.

The ability of the prepared strains (i.e., CJI9088, CJI9088_impE1(E164K), CJI9088impE2(V2I), CJI9088_impE2(G64E), and CJI9088_impE1(E164K)_ impE2(V2I)(G64D)) to produce IMP was evaluated. Upon completion of the culture, the amount of IMP production was measured by HPLC and the results are shown in Table 16 below.

TABLE 16

| Strain | IMP (g/L) |
|---|---|
| CJ9088 | 0.52 |
| CJ9088_impE1(E164K) | 0.84 |
| CJ9088_impE2(V2I) | 0.93 |
| CJ9088_impE2(G64E) | 1.73 |
| CJ9088_impE1(E164K)_impE2(V2I)(G64D) | 4.30 |

Upon confirming the amount of IMP accumulated in the culture medium, it was confirmed that these strains showed an increase of IMP production by at least 61%, and a maximum increase of 727%, compared to the parent strain, CJ9088. Accordingly, the increase in the amount of IMP production due to modifications of the ImpE protein of the present disclosure can be interpreted to be very meaningful.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polynucleotide encoding a protein variant, wherein the protein variant is capable of exporting 5'-inosine monophosphate and comprises an amino acid sequence that is identical to SEQ ID NO:2 except that (i) the 2nd amino acid, (ii) the 64th amino acid, or (iii) the 2nd amino acid and the 64th amino acid in the amino acid sequence of SEQ ID NO:2 are each substituted with another amino acid.

2. A vector comprising the polynucleotide of claim 1.

* * * * *

SEQUENCE LISTING

```
<160> NUMBER OF SEQ ID NOS: 154

<210> SEQ ID NO 1
<211> LENGTH: 222
<212> TYPE: PRT
<213> ORGANISM: Unknown
<220> FEATURE:
<223> OTHER INFORMATION: ImpE1

<400> SEQUENCE: 1

Leu His Ala Val Gln Glu Val Asn Asp Asn Glu Glu Asp Ser Leu Pro
1               5                   10                  15

Gly Ser Asp Leu Gly Leu Arg Glu Gln Lys Arg Leu Ala Thr Lys His
            20                  25                  30

Arg Ile Glu Asp Ala Ala Thr Arg Leu Val Asp Glu Ser Ser Phe Asp
        35                  40                  45

Lys Val Thr Ile Glu Glu Ile Cys Glu Ala Ala Gly Ile Ser Arg Arg
    50                  55                  60

Thr Phe Phe Asn Tyr Phe Ser Thr Lys Glu Ser Ala Val Ile Gly Ala
65                  70                  75                  80

Ser Ser Glu Pro Leu Thr Glu Lys Gln Arg Asn Asp Phe Leu Asn Ala
                85                  90                  95

Asp Ala Ser Asn Leu Leu Gln Leu Met Val Glu Gln Ile Lys Gln His
            100                 105                 110

Leu Glu Ser Ser His Gln Ser Gln Ala Ile His Asp Arg Arg Gln Arg
        115                 120                 125

Ile Phe Ala Asp Pro Asp Val Ala Val Arg Ala Met Ala Phe Arg Lys
    130                 135                 140

Glu Arg Ser Arg Glu Thr Met Glu Leu Ile Ala Gln Arg Leu Arg Glu
145                 150                 155                 160

His Pro Glu Glu Gln Arg Ala Pro Glu Leu Asp Pro Glu Thr Glu Ala
                165                 170                 175

Met Leu Leu Ser Gly Phe Ile Arg Glu Ala Thr Trp Met Ala Ile Ser
            180                 185                 190

Arg Pro Asp Arg Asp Cys Ala Leu Pro Val Gly Asp Arg Ile Tyr Arg
        195                 200                 205

Ala Met Glu Leu Val Lys Asn Tyr Thr Lys Gly Leu Glu Trp
    210                 215                 220

<210> SEQ ID NO 2
<211> LENGTH: 549
```

<212> TYPE: PRT
<213> ORGANISM: unknown
<220> FEATURE:
<223> OTHER INFORMATION: ImpE2

<400> SEQUENCE: 2

```
Met Val Ala Lys Asn Ser Thr Pro Ser Thr Ala Gly His Ala Ser Ala
1               5                   10                  15

His Thr Ala Glu Glu Phe Pro Val Ala Asn Ala Glu Met Ala Thr Pro
            20                  25                  30

Ser Ala Ile Asp Pro Asn His Gly Lys Lys Thr Ala Asp Asn Val Gly
        35                  40                  45

Ile Ile Phe Ala Ala Leu Met Leu Thr Met Leu Met Ser Ser Leu Gly
    50                  55                  60

Gln Met Ile Phe Gly Ser Ala Leu Pro Thr Ile Val Gly Glu Leu Gly
65                  70                  75                  80

Gly Val Asp Gln Met Ser Trp Val Ile Ser Ala Phe Met Val Thr Met
                85                  90                  95

Thr Ile Ala Met Pro Leu Ala Gly Gln Leu Gly Asp Arg Met Gly Arg
            100                 105                 110

Lys Trp Val Tyr Ile Ser Gly Ile Ser Ile Phe Val Ile Gly Ser Thr
        115                 120                 125

Leu Gly Gly Phe Ala Asn Gly Met Gly Met Leu Ile Thr Gly Arg Ala
    130                 135                 140

Ile Gln Gly Phe Gly Ala Gly Ile Met Met Ile Ser Ser Gln Ser Ile
145                 150                 155                 160

Val Ala Glu Val Val Ser Ala Arg Glu Arg Gly Lys Phe Met Gly Ile
                165                 170                 175

Met Gly Gly Val Phe Gly Val Ser Ser Val Leu Gly Pro Val Leu Gly
            180                 185                 190

Gly Trp Phe Thr Asp Gly Pro Gly Trp Arg Trp Gly Leu Trp Ile Asn
        195                 200                 205

Ile Pro Leu Gly Leu Leu Ala Ile Ile Val Cys Ala Phe Val Leu Lys
    210                 215                 220

Leu Arg Val Gly Glu Gln Gly Phe Lys Gly Phe Asp Trp Met Gly Phe
225                 230                 235                 240

Ala Ala Ile Ala Ile Thr Thr Ser Thr Leu Ile Leu Leu Thr Thr Trp
                245                 250                 255

Gly Gly Ser Glu Tyr Glu Trp Thr Ser Pro Thr Ile Leu Ser Met Ala
            260                 265                 270

Ala Val Val Ile Val Gly Ala Leu Leu Thr Val Phe Ile Glu Ser Arg
        275                 280                 285

Ala Ser Gln Pro Leu Ile Pro Val Gln Leu Phe Lys Asn Arg Asn Met
    290                 295                 300

Val Leu Thr Thr Leu Ala Gly Thr Val Leu Gly Leu Ala Met Met Gly
305                 310                 315                 320

Val Leu Gly Tyr Met Pro Thr Tyr Leu Gln Met Val His Thr Leu Thr
                325                 330                 335

Pro Thr Glu Ala Gly Leu Met Met Ile Pro Met Met Val Gly Met Ile
            340                 345                 350

Gly Val Ser Thr Gly Val Gly Phe Ile Ile Ala Lys Thr Gly Asn Tyr
        355                 360                 365

Lys Tyr Tyr Pro Ile Ala Gly Leu Ala Ile Thr Ala Phe Ala Leu Trp
    370                 375                 380
```

```
Trp Met Ser Gln Met Thr Val Glu Thr Ser Leu Thr Gly Ile Gly Val
385                 390                 395                 400

Arg Phe Leu Val Phe Gly Val Gly Leu Gly Phe Val Met Gln Val Leu
                405                 410                 415

Val Leu Ile Val Gln Asn Ser Phe Pro Val Ser Gln Val Gly Thr Ala
                420                 425                 430

Thr Ala Ala Asn Asn Phe Phe Arg Gln Ile Gly Ser Ala Leu Gly Ala
                435                 440                 445

Ser Ile Val Gly Ser Met Phe Ile His Asn Met Gln Asn Glu Met Ala
            450                 455                 460

Thr Arg Leu Pro Asp Ala Leu Ala Ser Leu Gly Lys Glu Gly Ala Ala
465                 470                 475                 480

Ile Ser Gln Gln Phe Gln Gly Ala Asp Ala Ala Asn Ser Leu Thr Pro
                485                 490                 495

His Ala Val Ala Glu Leu Pro Asp Val Leu Arg Asp Ala Ile Leu Asn
                500                 505                 510

Ser Tyr Asn Asp Gly Leu Thr Pro Val Ile Gly Met Met Val Pro Leu
                515                 520                 525

Ala Ile Val Ala Met Leu Ile Leu Phe Pro Leu Arg Gln Glu Arg Leu
530                 535                 540

Lys Glu Thr Ile Glu
545
```

<210> SEQ ID NO 3
<211> LENGTH: 669
<212> TYPE: DNA
<213> ORGANISM: unknown
<220> FEATURE:
<223> OTHER INFORMATION: ImpE1

<400> SEQUENCE: 3

```
ttgcatgctg tgcaagaagt taatgacaat gaagaagact ccctccctgg cagtgacctc      60
gggttaaggg agcagaagcg attggcaacc aagcatcgca tcgaagacgc cgcgacacgg     120
ttggttgatg aatcgagctt tgacaaagta acaattgaag aaatttgcga agccgccggg     180
atttcccgac gcacctttt  taattatttc agcacgaaag aaagcgccgt tattggcgcg     240
tcctcggaac cgttgacgga aaagcaacgc aatgacttct tgaatgctga cgccagcaat     300
ctcctgcagc tgatggttga gcagatcaaa caacacttgg agtcttctca ccagagtcaa     360
gcgattcacg accgtcgtca gcgaatcttt gcggatccgg atgtcgcggt acgtgcaatg     420
gcgtttcgca aggaacgctc acgggaaacc atggagctaa tcgctcaacg tcttcgggag     480
catcctgaag aacaacgcgc cccagaattg gatccggaaa cagaggcgat gctgctgagc     540
ggattcattc gcgaagccac ctggatggct atctcacgac ccgatcgtga ttgtgcactg     600
ccagtgggtg accgcatcta tcgcgcgatg gaattggtaa agaattacac gaaaggactg     660
gaatggtag                                                             669
```

<210> SEQ ID NO 4
<211> LENGTH: 1650
<212> TYPE: DNA
<213> ORGANISM: unknown
<220> FEATURE:
<223> OTHER INFORMATION: ImpE2

<400> SEQUENCE: 4

```
atggtagcta aaaactccac cccaagcacg gccggccacg ccagtgctca cactgcggaa      60
```

-continued

```
gaattcccag tggccaatgc tgaaatggca acgccttcag caatcgaccc aaaccacggt      120
aaaaagaccg cggataacgt cggcattatc ttcgctgcct tgatgctcac catgctgatg      180
agctctttgg ggcagatgat tttcggttcc gctctgccaa ccatcgtcgg cgagctcggc      240
ggcgtggacc agatgagctg gtaatttca  gcatttatgg tcaccatgac cattgctatg      300
ccactagccg gtcagctcgg tgaccgcatg gccgcaagt  gggtctacat ctcaggtatc      360
tccattttcg ttattggctc gacgctcggt ggctttgcca atggcatggg catgctgatc      420
accggacgtg caatccaggg cttcggtgcc ggcatcatga tgatttcctc gcagtcgatt      480
gtggctgagg ttgtctccgc acgtgagcgc ggcaagttca tgggtattat gggcggcgtc      540
tttggcgtct cctccgtact gggtccagtt ctcggtggct ggttcaccga tggtcccggt      600
tggcgttggg gcctgtggat caacattcca ctgggtctgc tggcaattat tgtctgcgct      660
ttcgtactga agctgcgcgt gggcgagcaa ggctttaagg gctttgactg gatgggtttt      720
gcggccatcg caatcacgac cagcaccctg attctgctca ccacttgggg cggaagcgaa      780
tacgagtgga cttccccaac tattttgtcc atggctgccg tagtcatcgt cggcgcgctg      840
ctcaccgtgt tcattgagtc gcgtgcatcc cagccgctga tcccggttca gctatttaag      900
aaccgcaaca tggttttgac caccctcgcc ggtactgttt gggtctggc  catgatgggc      960 gtgctcggct acatgccaac ctacctgcag atggtgcaca ccctgacgcc aactgaagca     1020
ggcttgatga tgatcccgat gatggtcggc atgatcggtg tctccactgg tgttggcttc     1080
atcatcgcta agaccggcaa ctacaagtac taccccatcg cgggcctggc catcacggcg     1140
tttgctttgt ggtggatgtc ccagatgacc gttgagactt cattgaccgg tatcggagtt     1200
cgcttccttg tattcggtgt cggcttgggc tttgtcatgc aggtactggt gctgattgtt     1260
caaaactcct tccctgtatc gcaggtcggt actgccacgg cggctaataa cttcttccgc     1320
cagattggtt cggcattggg tgcttccatc gtgggttcga tgttcattca caatatgcag     1380
aatgagatgg ctacccgttt gcctgatgcc cttgcatcgt tgggcaagga aggcgccgct     1440
atttcgcagc agttccaagg tgcagatgcc gccaactcct tgactccgca cgcagtcgca     1500
gagcttcccg atgtcctccg tgacgctatc ttaaattcct acaatgacgg tctgaccccc     1560
gtgattggca tgatggtgcc actggccatt gttgcaatgc tgattttgtt cccactgcgc     1620
caagagcgct tgaaggaaac catcgaataa                                      1650
```

<210> SEQ ID NO 5
<211> LENGTH: 29
<212> TYPE: DNA
<213> ORGANISM: Artificial Sequence
<220> FEATURE:
<223> OTHER INFORMATION: Primer impE1 kop-1

<400> SEQUENCE: 5

```
gctctagacg agaaagctaa agccggtga                                         29
```

<210> SEQ ID NO 6
<211> LENGTH: 36
<212> TYPE: DNA
<213> ORGANISM: Artificial Sequence
<220> FEATURE:
<223> OTHER INFORMATION: Primer impE1 kop-2

<400> SEQUENCE: 6

```
gtttttagct accattgtta caccccgtgc aagttt                                 36
```

```
<210> SEQ ID NO 7
<211> LENGTH: 36
<212> TYPE: DNA
<213> ORGANISM: Artificial Sequence
<220> FEATURE:
<223> OTHER INFORMATION: Primer impE1 kop-3

<400> SEQUENCE: 7
gcacggggtg taacaatggt agctaaaaac tccacc                              36

<210> SEQ ID NO 8
<211> LENGTH: 29
<212> TYPE: DNA
<213> ORGANISM: Artificial Sequence
<220> FEATURE:
<223> OTHER INFORMATION: Primer impE1 kop-4

<400> SEQUENCE: 8
gctctagaaa tagttgggga agtccactc                                      29

<210> SEQ ID NO 9
<211> LENGTH: 29
<212> TYPE: DNA
<213> ORGANISM: Artificial Sequence
<220> FEATURE:
<223> OTHER INFORMATION: Primer impE2 kop-1

<400> SEQUENCE: 9
gctctagact tggatgacct ggtggaaaa                                      29

<210> SEQ ID NO 10
<211> LENGTH: 36
<212> TYPE: DNA
<213> ORGANISM: Artificial Sequence
<220> FEATURE:
<223> OTHER INFORMATION: Primer impE2 kop-2

<400> SEQUENCE: 10
cttggagaaa atttcctacc attccagtcc tttcgt                              36

<210> SEQ ID NO 11
<211> LENGTH: 36
<212> TYPE: DNA
<213> ORGANISM: Artificial Sequence
<220> FEATURE:
<223> OTHER INFORMATION: Primer impE2 kop-3

<400> SEQUENCE: 11
ggactggaat ggtaggaaat tttctccaag ggaaat                              36

<210> SEQ ID NO 12
<211> LENGTH: 29
<212> TYPE: DNA
<213> ORGANISM: Artificial Sequence
<220> FEATURE:
<223> OTHER INFORMATION: Primer impE2 kop-4

<400> SEQUENCE: 12
ggactagtgg attgtgttga cgcacgatg                                      29

<210> SEQ ID NO 13
<211> LENGTH: 36
<212> TYPE: DNA
<213> ORGANISM: Artificial Sequence
<220> FEATURE:
<223> OTHER INFORMATION: Primer impE1E2 kop-2
```

```
<400> SEQUENCE: 13
cttggagaaa atttctgtta caccccgtgc aagttt                              36

<210> SEQ ID NO 14
<211> LENGTH: 36
<212> TYPE: DNA
<213> ORGANISM: Artificial Sequence
<220> FEATURE:
<223> OTHER INFORMATION: Primer impE1E2 kop-3

<400> SEQUENCE: 14
gcacggggtg taacagaaat tttctccaag ggaaat                              36

<210> SEQ ID NO 15
<211> LENGTH: 21
<212> TYPE: DNA
<213> ORGANISM: Artificial Sequence
<220> FEATURE:
<223> OTHER INFORMATION: Primer impE1E2 seqF

<400> SEQUENCE: 15
gaacggagtc atctcctttg c                                              21

<210> SEQ ID NO 16
<211> LENGTH: 22
<212> TYPE: DNA
<213> ORGANISM: Artificial Sequence
<220> FEATURE:
<223> OTHER INFORMATION: Primer impE1E2 seqR

<400> SEQUENCE: 16
ccaaacgctc tgcaagaaac tg                                             22

<210> SEQ ID NO 17
<211> LENGTH: 29
<212> TYPE: DNA
<213> ORGANISM: Artificial Sequence
<220> FEATURE:
<223> OTHER INFORMATION: Primer impE1E2 WT F

<400> SEQUENCE: 17
gctctagaga acggagtcat ctcctttgc                                      29

<210> SEQ ID NO 18
<211> LENGTH: 30
<212> TYPE: DNA
<213> ORGANISM: Artificial Sequence
<220> FEATURE:
<223> OTHER INFORMATION: Primer impE1E2 WT R

<400> SEQUENCE: 18
gctctagacc aaacgctctg caagaaactg                                     30

<210> SEQ ID NO 19
<211> LENGTH: 29
<212> TYPE: DNA
<213> ORGANISM: Artificial Sequence
<220> FEATURE:
<223> OTHER INFORMATION: Primer impE1 164K-1

<400> SEQUENCE: 19
gctctagact tggatgacct ggtggaaaa                                      29

<210> SEQ ID NO 20
<211> LENGTH: 37
```

<210> SEQ ID NO 20
<211> LENGTH: 37
<212> TYPE: DNA
<213> ORGANISM: Artificial Sequence
<220> FEATURE:
<223> OTHER INFORMATION: Primer impE1 164K-2

<400> SEQUENCE: 20
ctggggcgcg ttgtttttca ggatgctccc gaagacg                              37

<210> SEQ ID NO 21
<211> LENGTH: 21
<212> TYPE: DNA
<213> ORGANISM: Artificial Sequence
<220> FEATURE:
<223> OTHER INFORMATION: Primer impE1 164K-3

<400> SEQUENCE: 21
aacaacgcgc cccagaattg g                                               21

<210> SEQ ID NO 22
<211> LENGTH: 29
<212> TYPE: DNA
<213> ORGANISM: Artificial Sequence
<220> FEATURE:
<223> OTHER INFORMATION: Primer impE1 164K-4

<400> SEQUENCE: 22
gctctagaaa tagttgggga agtccactc                                       29

<210> SEQ ID NO 23
<211> LENGTH: 37
<212> TYPE: DNA
<213> ORGANISM: Artificial Sequence
<220> FEATURE:
<223> OTHER INFORMATION: Primer impE2 V2I-2

<400> SEQUENCE: 23
tggagttttt agctatcatt ccagtccttt cgtgtaa                              37

<210> SEQ ID NO 24
<211> LENGTH: 21
<212> TYPE: DNA
<213> ORGANISM: Artificial Sequence
<220> FEATURE:
<223> OTHER INFORMATION: Primer impE2 V2I-3

<400> SEQUENCE: 24
tagctaaaaa ctccacccca a                                               21

<210> SEQ ID NO 25
<211> LENGTH: 37
<212> TYPE: DNA
<213> ORGANISM: Artificial Sequence
<220> FEATURE:
<223> OTHER INFORMATION: Primer impE2 G64E-2

<400> SEQUENCE: 25
ccgaaaatca tctgctccaa agagctcatc agcatgg                              37

<210> SEQ ID NO 26
<211> LENGTH: 21
<212> TYPE: DNA
<213> ORGANISM: Artificial Sequence
<220> FEATURE:
<223> OTHER INFORMATION: Primer impE2 G64E-3

<400> SEQUENCE: 26
gcagatgatt ttcggttccg c						21

<210> SEQ ID NO 27
<211> LENGTH: 27
<212> TYPE: DNA
<213> ORGANISM: Artificial Sequence
<220> FEATURE:
<223> OTHER INFORMATION: Primer Spe1-impE1 164 1F

<400> SEQUENCE: 27
gggactagtg attccggcca actgtcg					27

<210> SEQ ID NO 28
<211> LENGTH: 27
<212> TYPE: DNA
<213> ORGANISM: Artificial Sequence
<220> FEATURE:
<223> OTHER INFORMATION: Primer impE1 164-R 1R

<400> SEQUENCE: 28
tggggcgcgt tggcgttcag gatgctc					27

<210> SEQ ID NO 29
<211> LENGTH: 27
<212> TYPE: DNA
<213> ORGANISM: Artificial Sequence
<220> FEATURE:
<223> OTHER INFORMATION: Primer impE1 164-H 1R

<400> SEQUENCE: 29
tggggcgcgt tggtgttcag gatgctc					27

<210> SEQ ID NO 30
<211> LENGTH: 27
<212> TYPE: DNA
<213> ORGANISM: Artificial Sequence
<220> FEATURE:
<223> OTHER INFORMATION: Primer impE1 164-D 1R

<400> SEQUENCE: 30
tggggcgcgt tgatcttcag gatgctc					27

<210> SEQ ID NO 31
<211> LENGTH: 27
<212> TYPE: DNA
<213> ORGANISM: Artificial Sequence
<220> FEATURE:
<223> OTHER INFORMATION: Primer impE1 164-S 1R

<400> SEQUENCE: 31
tggggcgcgt tgggattcag gatgctc					27

<210> SEQ ID NO 32
<211> LENGTH: 27
<212> TYPE: DNA
<213> ORGANISM: Artificial Sequence
<220> FEATURE:
<223> OTHER INFORMATION: Primer impE1 164-T 1R

<400> SEQUENCE: 32
tggggcgcgt tgggtttcag gatgctc					27

<210> SEQ ID NO 33
<211> LENGTH: 27
<212> TYPE: DNA
<213> ORGANISM: Artificial Sequence -continued

```
<220> FEATURE:
<223> OTHER INFORMATION: Primer impE1 164-N 1R

<400> SEQUENCE: 33
tggggcgcgt tggttttcag gatgctc                                          27

<210> SEQ ID NO 34
<211> LENGTH: 27
<212> TYPE: DNA
<213> ORGANISM: Artificial Sequence
<220> FEATURE:
<223> OTHER INFORMATION: Primer impE1 164-Q 1R

<400> SEQUENCE: 34
tggggcgcgt tgctgttcag gatgctc                                          27

<210> SEQ ID NO 35
<211> LENGTH: 27
<212> TYPE: DNA
<213> ORGANISM: Artificial Sequence
<220> FEATURE:
<223> OTHER INFORMATION: Primer impE1 164-C 1R

<400> SEQUENCE: 35
tggggcgcgt tggcattcag gatgctc                                          27

<210> SEQ ID NO 36
<211> LENGTH: 27
<212> TYPE: DNA
<213> ORGANISM: Artificial Sequence
<220> FEATURE:
<223> OTHER INFORMATION: Primer impE1 164-G 1R

<400> SEQUENCE: 36
tggggcgcgt tggccttcag gatgctc                                          27

<210> SEQ ID NO 37
<211> LENGTH: 27
<212> TYPE: DNA
<213> ORGANISM: Artificial Sequence
<220> FEATURE:
<223> OTHER INFORMATION: Primer impE1 164-P 1R

<400> SEQUENCE: 37
tggggcgcgt tgcggttcag gatgctc                                          27

<210> SEQ ID NO 38
<211> LENGTH: 27
<212> TYPE: DNA
<213> ORGANISM: Artificial Sequence
<220> FEATURE:
<223> OTHER INFORMATION: Primer impE1 164-A 1R

<400> SEQUENCE: 38
tggggcgcgt tgggcttcag gatgctc                                          27

<210> SEQ ID NO 39
<211> LENGTH: 27
<212> TYPE: DNA
<213> ORGANISM: Artificial Sequence
<220> FEATURE:
<223> OTHER INFORMATION: Primer impE1 164-V 1R

<400> SEQUENCE: 39
tggggcgcgt tggacttcag gatgctc                                          27
```

```
<210> SEQ ID NO 40
<211> LENGTH: 27
<212> TYPE: DNA
<213> ORGANISM: Artificial Sequence
<220> FEATURE:
<223> OTHER INFORMATION: Primer impE1 164-I 1R

<400> SEQUENCE: 40
tggggcgcgt tggatttcag gatgctc                                              27

<210> SEQ ID NO 41
<211> LENGTH: 27
<212> TYPE: DNA
<213> ORGANISM: Artificial Sequence
<220> FEATURE:
<223> OTHER INFORMATION: Primer impE1 164-L 1R

<400> SEQUENCE: 41
tggggcgcgt tgcagttcag gatgctc                                              27

<210> SEQ ID NO 42
<211> LENGTH: 27
<212> TYPE: DNA
<213> ORGANISM: Artificial Sequence
<220> FEATURE:
<223> OTHER INFORMATION: Primer impE1 164-M 1R

<400> SEQUENCE: 42
tggggcgcgt tgcatttcag gatgctc                                              27

<210> SEQ ID NO 43
<211> LENGTH: 27
<212> TYPE: DNA
<213> ORGANISM: Artificial Sequence
<220> FEATURE:
<223> OTHER INFORMATION: Primer impE1 164-F 1R

<400> SEQUENCE: 43
tggggcgcgt tggaattcag gatgctc                                              27

<210> SEQ ID NO 44
<211> LENGTH: 27
<212> TYPE: DNA
<213> ORGANISM: Artificial Sequence
<220> FEATURE:
<223> OTHER INFORMATION: Primer impE1 164-Y 1R

<400> SEQUENCE: 44
tggggcgcgt tggtattcag gatgctc                                              27

<210> SEQ ID NO 45
<211> LENGTH: 27
<212> TYPE: DNA
<213> ORGANISM: Artificial Sequence
<220> FEATURE:
<223> OTHER INFORMATION: Primer impE1 164-W 1R

<400> SEQUENCE: 45
tggggcgcgt tgccattcag gatgctc                                              27

<210> SEQ ID NO 46
<211> LENGTH: 27
<212> TYPE: DNA
<213> ORGANISM: Artificial Sequence
<220> FEATURE:
<223> OTHER INFORMATION: Primer Spe1-impE1 164 2R
```

```
<400> SEQUENCE: 46
gggactagtc atgaacttgc cgcgctc                                              27

<210> SEQ ID NO 47
<211> LENGTH: 27
<212> TYPE: DNA
<213> ORGANISM: Artificial Sequence
<220> FEATURE:
<223> OTHER INFORMATION: Primer impE1 164-R 2F

<400> SEQUENCE: 47
gagcatcctg aacgccaacg cgcccca                                              27

<210> SEQ ID NO 48
<211> LENGTH: 27
<212> TYPE: DNA
<213> ORGANISM: Artificial Sequence
<220> FEATURE:
<223> OTHER INFORMATION: Primer impE1 164-H 2F

<400> SEQUENCE: 48
gagcatcctg aacaccaacg cgcccca                                              27

<210> SEQ ID NO 49
<211> LENGTH: 27
<212> TYPE: DNA
<213> ORGANISM: Artificial Sequence
<220> FEATURE:
<223> OTHER INFORMATION: Primer impE1 164-D 2F

<400> SEQUENCE: 49
gagcatcctg aagatcaacg cgcccca                                              27

<210> SEQ ID NO 50
<211> LENGTH: 27
<212> TYPE: DNA
<213> ORGANISM: Artificial Sequence
<220> FEATURE:
<223> OTHER INFORMATION: Primer impE1 164-S 2F

<400> SEQUENCE: 50
gagcatcctg aatcccaacg cgcccca                                              27

<210> SEQ ID NO 51
<211> LENGTH: 27
<212> TYPE: DNA
<213> ORGANISM: Artificial Sequence
<220> FEATURE:
<223> OTHER INFORMATION: Primer impE1 164-T 2F

<400> SEQUENCE: 51
gagcatcctg aaacccaacg cgcccca                                              27

<210> SEQ ID NO 52
<211> LENGTH: 27
<212> TYPE: DNA
<213> ORGANISM: Artificial Sequence
<220> FEATURE:
<223> OTHER INFORMATION: Primer impE1 164-N 2F

<400> SEQUENCE: 52
gagcatcctg aaaaccaacg cgcccca                                              27

<210> SEQ ID NO 53
```

```
<211> LENGTH: 27
<212> TYPE: DNA
<213> ORGANISM: Artificial Sequence
<220> FEATURE:
<223> OTHER INFORMATION: Primer impE1 164-Q 2F

<400> SEQUENCE: 53
gagcatcctg aacagcaacg cgcccca                                              27

<210> SEQ ID NO 54
<211> LENGTH: 27
<212> TYPE: DNA
<213> ORGANISM: Artificial Sequence
<220> FEATURE:
<223> OTHER INFORMATION: Primer impE1 164-C 2F

<400> SEQUENCE: 54
gagcatcctg aatgccaacg cgcccca                                              27

<210> SEQ ID NO 55
<211> LENGTH: 27
<212> TYPE: DNA
<213> ORGANISM: Artificial Sequence
<220> FEATURE:
<223> OTHER INFORMATION: Primer impE1 164-G 2F

<400> SEQUENCE: 55
gagcatcctg aaggccaacg cgcccca                                              27

<210> SEQ ID NO 56
<211> LENGTH: 27
<212> TYPE: DNA
<213> ORGANISM: Artificial Sequence
<220> FEATURE:
<223> OTHER INFORMATION: Primer impE1 164-P 2F

<400> SEQUENCE: 56
gagcatcctg aaccgcaacg cgcccca                                              27

<210> SEQ ID NO 57
<211> LENGTH: 27
<212> TYPE: DNA
<213> ORGANISM: Artificial Sequence
<220> FEATURE:
<223> OTHER INFORMATION: Primer impE1 164-A 2F

<400> SEQUENCE: 57
gagcatcctg aagcccaacg cgcccca                                              27

<210> SEQ ID NO 58
<211> LENGTH: 27
<212> TYPE: DNA
<213> ORGANISM: Artificial Sequence
<220> FEATURE:
<223> OTHER INFORMATION: Primer impE1 164-V 2F

<400> SEQUENCE: 58
gagcatcctg aagtccaacg cgcccca                                              27

<210> SEQ ID NO 59
<211> LENGTH: 27
<212> TYPE: DNA
<213> ORGANISM: Artificial Sequence
<220> FEATURE:
<223> OTHER INFORMATION: Primer impE1 164-I 2F

<400> SEQUENCE: 59
```

```
gagcatcctg aaatccaacg cgcccca                                         27
```

<210> SEQ ID NO 60
<211> LENGTH: 27
<212> TYPE: DNA
<213> ORGANISM: Artificial Sequence
<220> FEATURE:
<223> OTHER INFORMATION: Primer impE1 164-L 2F

<400> SEQUENCE: 60

```
gagcatcctg aactgcaacg cgcccca                                         27
```

<210> SEQ ID NO 61
<211> LENGTH: 27
<212> TYPE: DNA
<213> ORGANISM: Artificial Sequence
<220> FEATURE:
<223> OTHER INFORMATION: Primer impE1 164-M 2F

<400> SEQUENCE: 61

```
gagcatcctg aaatgcaacg cgcccca                                         27
```

<210> SEQ ID NO 62
<211> LENGTH: 27
<212> TYPE: DNA
<213> ORGANISM: Artificial Sequence
<220> FEATURE:
<223> OTHER INFORMATION: Primer impE1 164-F 2F

<400> SEQUENCE: 62

```
gagcatcctg aattccaacg cgcccca                                         27
```

<210> SEQ ID NO 63
<211> LENGTH: 27
<212> TYPE: DNA
<213> ORGANISM: Artificial Sequence
<220> FEATURE:
<223> OTHER INFORMATION: Primer impE1 164-Y 2F

<400> SEQUENCE: 63

```
gagcatcctg aataccaacg cgcccca                                         27
```

<210> SEQ ID NO 64
<211> LENGTH: 27
<212> TYPE: DNA
<213> ORGANISM: Artificial Sequence
<220> FEATURE:
<223> OTHER INFORMATION: Primer impE1 164-W 2F

<400> SEQUENCE: 64

```
gagcatcctg aatggcaacg cgcccca                                         27
```

<210> SEQ ID NO 65
<211> LENGTH: 26
<212> TYPE: DNA
<213> ORGANISM: Artificial Sequence
<220> FEATURE:
<223> OTHER INFORMATION: Primer XbaI-impE2 2 1F

<400> SEQUENCE: 65

```
gggtctagat tgcatgctgt gcaaga                                          26
```

<210> SEQ ID NO 66
<211> LENGTH: 27
<212> TYPE: DNA

<213> ORGANISM: Artificial Sequence
<220> FEATURE:
<223> OTHER INFORMATION: Primer impE2 2-R 1R

<400> SEQUENCE: 66
ggagttttta gcgcgcattc cagtcct                                        27

<210> SEQ ID NO 67
<211> LENGTH: 27
<212> TYPE: DNA
<213> ORGANISM: Artificial Sequence
<220> FEATURE:
<223> OTHER INFORMATION: Primer impE2 2-H 1R

<400> SEQUENCE: 67
ggagttttta gcgtgcattc cagtcct                                        27

<210> SEQ ID NO 68
<211> LENGTH: 27
<212> TYPE: DNA
<213> ORGANISM: Artificial Sequence
<220> FEATURE:
<223> OTHER INFORMATION: Primer impE2 2-K 1R

<400> SEQUENCE: 68
ggagttttta gccttcattc cagtcct                                        27

<210> SEQ ID NO 69
<211> LENGTH: 27
<212> TYPE: DNA
<213> ORGANISM: Artificial Sequence
<220> FEATURE:
<223> OTHER INFORMATION: Primer impE2 2-D 1R

<400> SEQUENCE: 69
ggagttttta gcgtccattc cagtcct                                        27

<210> SEQ ID NO 70
<211> LENGTH: 27
<212> TYPE: DNA
<213> ORGANISM: Artificial Sequence
<220> FEATURE:
<223> OTHER INFORMATION: Primer impE2 2-E 1R

<400> SEQUENCE: 70
ggagttttta gcttccattc cagtcct                                        27

<210> SEQ ID NO 71
<211> LENGTH: 27
<212> TYPE: DNA
<213> ORGANISM: Artificial Sequence
<220> FEATURE:
<223> OTHER INFORMATION: Primer impE2 2-S 1R

<400> SEQUENCE: 71
ggagttttta gcggacattc cagtcct                                        27

<210> SEQ ID NO 72
<211> LENGTH: 27
<212> TYPE: DNA
<213> ORGANISM: Artificial Sequence
<220> FEATURE:
<223> OTHER INFORMATION: Primer impE2 2-T 1R

<400> SEQUENCE: 72
ggagttttta gcggtcattc cagtcct                                        27

<210> SEQ ID NO 73
<211> LENGTH: 27
<212> TYPE: DNA
<213> ORGANISM: Artificial Sequence
<220> FEATURE:
<223> OTHER INFORMATION: Primer impE2 2-N 1R

<400> SEQUENCE: 73
ggagttttta gcgttcattc cagtcct                                            27

<210> SEQ ID NO 74
<211> LENGTH: 27
<212> TYPE: DNA
<213> ORGANISM: Artificial Sequence
<220> FEATURE:
<223> OTHER INFORMATION: Primer impE2 2-Q 1R

<400> SEQUENCE: 74
ggagttttta gcctgcattc cagtcct                                            27

<210> SEQ ID NO 75
<211> LENGTH: 27
<212> TYPE: DNA
<213> ORGANISM: Artificial Sequence
<220> FEATURE:
<223> OTHER INFORMATION: Primer impE2 2-C 1R

<400> SEQUENCE: 75
ggagttttta gcgcacattc cagtcct                                            27

<210> SEQ ID NO 76
<211> LENGTH: 27
<212> TYPE: DNA
<213> ORGANISM: Artificial Sequence
<220> FEATURE:
<223> OTHER INFORMATION: Primer impE2 2-G 1R

<400> SEQUENCE: 76
ggagttttta gcgcccattc cagtcct                                            27

<210> SEQ ID NO 77
<211> LENGTH: 27
<212> TYPE: DNA
<213> ORGANISM: Artificial Sequence
<220> FEATURE:
<223> OTHER INFORMATION: Primer impE2 2-P 1R

<400> SEQUENCE: 77
ggagttttta gctggcattc cagtcct                                            27

<210> SEQ ID NO 78
<211> LENGTH: 27
<212> TYPE: DNA
<213> ORGANISM: Artificial Sequence
<220> FEATURE:
<223> OTHER INFORMATION: Primer impE2 2-A 1R

<400> SEQUENCE: 78
ggagttttta gcagccattc cagtcct                                            27

<210> SEQ ID NO 79
<211> LENGTH: 27
<212> TYPE: DNA
<213> ORGANISM: Artificial Sequence
<220> FEATURE:

<223> OTHER INFORMATION: Primer impE2 2-L 1R

<400> SEQUENCE: 79 ggagtttttα gccagcattc cagtcct                                              27

<210> SEQ ID NO 80
<211> LENGTH: 27
<212> TYPE: DNA
<213> ORGANISM: Artificial Sequence
<220> FEATURE:
<223> OTHER INFORMATION: Primer impE2 2-M 1R

<400> SEQUENCE: 80 ggagtttttα gccatcattc cagtcct                                              27

<210> SEQ ID NO 81
<211> LENGTH: 27
<212> TYPE: DNA
<213> ORGANISM: Artificial Sequence
<220> FEATURE:
<223> OTHER INFORMATION: Primer impE2 2-F 1R

<400> SEQUENCE: 81 ggagtttttα gcgaacattc cagtcct                                              27

<210> SEQ ID NO 82
<211> LENGTH: 27
<212> TYPE: DNA
<213> ORGANISM: Artificial Sequence
<220> FEATURE:
<223> OTHER INFORMATION: Primer impE2 2-Y 1R

<400> SEQUENCE: 82 ggagtttttα gcgtacattc cagtcct                                              27

<210> SEQ ID NO 83
<211> LENGTH: 27
<212> TYPE: DNA
<213> ORGANISM: Artificial Sequence
<220> FEATURE:
<223> OTHER INFORMATION: Primer impE2 2-W 1R

<400> SEQUENCE: 83 ggagtttttα gcccacattc cagtcct                                              27

<210> SEQ ID NO 84
<211> LENGTH: 26
<212> TYPE: DNA
<213> ORGANISM: Artificial Sequence
<220> FEATURE:
<223> OTHER INFORMATION: Primer XbaI-impE2 2 2R

<400> SEQUENCE: 84
gggtctagat tgctcgccca cgcgca                                               26

<210> SEQ ID NO 85
<211> LENGTH: 27
<212> TYPE: DNA
<213> ORGANISM: Artificial Sequence
<220> FEATURE:
<223> OTHER INFORMATION: Primer impE2 2-R 2F

<400> SEQUENCE: 85
aggactggaa tgcgcgctaa aaactcc                                              27

```
<210> SEQ ID NO 86
<211> LENGTH: 27
<212> TYPE: DNA
<213> ORGANISM: Artificial Sequence
<220> FEATURE:
<223> OTHER INFORMATION: Primer impE2 2-H 2F

<400> SEQUENCE: 86
aggactggaa tgcacgctaa aaactcc                                            27

<210> SEQ ID NO 87
<211> LENGTH: 27
<212> TYPE: DNA
<213> ORGANISM: Artificial Sequence
<220> FEATURE:
<223> OTHER INFORMATION: Primer impE2 2-K 2F

<400> SEQUENCE: 87
aggactggaa tgaaggctaa aaactcc                                            27

<210> SEQ ID NO 88
<211> LENGTH: 27
<212> TYPE: DNA
<213> ORGANISM: Artificial Sequence
<220> FEATURE:
<223> OTHER INFORMATION: Primer impE2 2-D 2F

<400> SEQUENCE: 88
aggactggaa tggacgctaa aaactcc                                            27

<210> SEQ ID NO 89
<211> LENGTH: 27
<212> TYPE: DNA
<213> ORGANISM: Artificial Sequence
<220> FEATURE:
<223> OTHER INFORMATION: Primer impE2 2-E 2F

<400> SEQUENCE: 89
aggactggaa tggaagctaa aaactcc                                            27

<210> SEQ ID NO 90
<211> LENGTH: 27
<212> TYPE: DNA
<213> ORGANISM: Artificial Sequence
<220> FEATURE:
<223> OTHER INFORMATION: Primer impE2 2-S 2F

<400> SEQUENCE: 90
aggactggaa tgtccgctaa aaactcc                                            27

<210> SEQ ID NO 91
<211> LENGTH: 27
<212> TYPE: DNA
<213> ORGANISM: Artificial Sequence
<220> FEATURE:
<223> OTHER INFORMATION: Primer impE2 2-T 2F

<400> SEQUENCE: 91
aggactggaa tgaccgctaa aaactcc                                            27

<210> SEQ ID NO 92
<211> LENGTH: 27
<212> TYPE: DNA
<213> ORGANISM: Artificial Sequence
<220> FEATURE:
<223> OTHER INFORMATION: Primer impE2 2-N 2F
```

<400> SEQUENCE: 92
aggactggaa tgaacgctaa aaactcc         27

<210> SEQ ID NO 93
<211> LENGTH: 27
<212> TYPE: DNA
<213> ORGANISM: Artificial Sequence
<220> FEATURE:
<223> OTHER INFORMATION: Primer impE2 2-Q 2F

<400> SEQUENCE: 93
aggactggaa tgcaggctaa aaactcc         27

<210> SEQ ID NO 94
<211> LENGTH: 27
<212> TYPE: DNA
<213> ORGANISM: Artificial Sequence
<220> FEATURE:
<223> OTHER INFORMATION: Primer impE2 2-C 2F

<400> SEQUENCE: 94
aggactggaa tgtgcgctaa aaactcc         27

<210> SEQ ID NO 95
<211> LENGTH: 27
<212> TYPE: DNA
<213> ORGANISM: Artificial Sequence
<220> FEATURE:
<223> OTHER INFORMATION: Primer impE2 2-G 2F

<400> SEQUENCE: 95
aggactggaa tgggcgctaa aaactcc         27

<210> SEQ ID NO 96
<211> LENGTH: 27
<212> TYPE: DNA
<213> ORGANISM: Artificial Sequence
<220> FEATURE:
<223> OTHER INFORMATION: Primer impE2 2-P 2F

<400> SEQUENCE: 96
aggactggaa tgccagctaa aaactcc         27

<210> SEQ ID NO 97
<211> LENGTH: 27
<212> TYPE: DNA
<213> ORGANISM: Artificial Sequence
<220> FEATURE:
<223> OTHER INFORMATION: Primer impE2 2-A 2F

<400> SEQUENCE: 97
aggactggaa tggctgctaa aaactcc         27

<210> SEQ ID NO 98
<211> LENGTH: 27
<212> TYPE: DNA
<213> ORGANISM: Artificial Sequence
<220> FEATURE:
<223> OTHER INFORMATION: Primer impE2 2-L 2F

<400> SEQUENCE: 98
aggactggaa tgctggctaa aaactcc         27

<210> SEQ ID NO 99
<211> LENGTH: 27

<210> SEQ ID NO 99
<211> LENGTH: 27
<212> TYPE: DNA
<213> ORGANISM: Artificial Sequence
<220> FEATURE:
<223> OTHER INFORMATION: Primer impE2 2-M 2F

<400> SEQUENCE: 99
aggactggaa tgatggctaa aaactcc                                              27

<210> SEQ ID NO 100
<211> LENGTH: 27
<212> TYPE: DNA
<213> ORGANISM: Artificial Sequence
<220> FEATURE:
<223> OTHER INFORMATION: Primer impE2 2-F 2F

<400> SEQUENCE: 100
aggactggaa tgttcgctaa aaactcc                                              27

<210> SEQ ID NO 101
<211> LENGTH: 27
<212> TYPE: DNA
<213> ORGANISM: Artificial Sequence
<220> FEATURE:
<223> OTHER INFORMATION: Primer impE2 2-Y 2F

<400> SEQUENCE: 101
aggactggaa tgtacgctaa aaactcc                                              27

<210> SEQ ID NO 102
<211> LENGTH: 27
<212> TYPE: DNA
<213> ORGANISM: Artificial Sequence
<220> FEATURE:
<223> OTHER INFORMATION: Primer impE2 2-W 2F

<400> SEQUENCE: 102
aggactggaa tgtgggctaa aaactcc                                              27

<210> SEQ ID NO 103
<211> LENGTH: 30
<212> TYPE: DNA
<213> ORGANISM: Artificial Sequence
<220> FEATURE:
<223> OTHER INFORMATION: Primer XbaI-impE2 64 1F

<400> SEQUENCE: 103
gggtctagaa aagagcttaa ggcagctgct                                           30

<210> SEQ ID NO 104
<211> LENGTH: 27
<212> TYPE: DNA
<213> ORGANISM: Artificial Sequence
<220> FEATURE:
<223> OTHER INFORMATION: Primer impE2 64-R 1R

<400> SEQUENCE: 104
gaaaatcatc tggcgcaaag agctcat                                              27

<210> SEQ ID NO 105
<211> LENGTH: 27
<212> TYPE: DNA
<213> ORGANISM: Artificial Sequence
<220> FEATURE:
<223> OTHER INFORMATION: Primer impE2 64-H 1R

<400> SEQUENCE: 105
gaaaatcatc tggtgcaaag agctcat        27

<210> SEQ ID NO 106
<211> LENGTH: 27
<212> TYPE: DNA
<213> ORGANISM: Artificial Sequence
<220> FEATURE:
<223> OTHER INFORMATION: Primer impE2 64-D 1R

<400> SEQUENCE: 106
gaaaatcatc tggtccaaag agctcat        27

<210> SEQ ID NO 107
<211> LENGTH: 27
<212> TYPE: DNA
<213> ORGANISM: Artificial Sequence
<220> FEATURE:
<223> OTHER INFORMATION: Primer impE2 64-K 1R

<400> SEQUENCE: 107
gaaaatcatc tgcttcaaag agctcat        27

<210> SEQ ID NO 108
<211> LENGTH: 27
<212> TYPE: DNA
<213> ORGANISM: Artificial Sequence
<220> FEATURE:
<223> OTHER INFORMATION: Primer impE2 64-S 1R

<400> SEQUENCE: 108
gaaaatcatc tgggacaaag agctcat        27

<210> SEQ ID NO 109
<211> LENGTH: 27
<212> TYPE: DNA
<213> ORGANISM: Artificial Sequence
<220> FEATURE:
<223> OTHER INFORMATION: Primer impE2 64-T 1R

<400> SEQUENCE: 109
gaaaatcatc tgggtcaaag agctcat        27

<210> SEQ ID NO 110
<211> LENGTH: 27
<212> TYPE: DNA
<213> ORGANISM: Artificial Sequence
<220> FEATURE:
<223> OTHER INFORMATION: Primer impE2 64-N 1R

<400> SEQUENCE: 110
gaaaatcatc tggttcaaag agctcat        27

<210> SEQ ID NO 111
<211> LENGTH: 27
<212> TYPE: DNA
<213> ORGANISM: Artificial Sequence
<220> FEATURE:
<223> OTHER INFORMATION: Primer impE2 64-Q 1R

<400> SEQUENCE: 111
gaaaatcatc tgctgcaaag agctcat        27

<210> SEQ ID NO 112
<211> LENGTH: 27
<212> TYPE: DNA
<213> ORGANISM: Artificial Sequence
<220> FEATURE:
<223> OTHER INFORMATION: Primer impE2 64-C 1R

<400> SEQUENCE: 112
gaaaatcatc tggcacaaag agctcat        27

<210> SEQ ID NO 113
<211> LENGTH: 27
<212> TYPE: DNA
<213> ORGANISM: Artificial Sequence
<220> FEATURE:
<223> OTHER INFORMATION: Primer impE2 64-P 1R

<400> SEQUENCE: 113
gaaaatcatc tgtggcaaag agctcat        27

<210> SEQ ID NO 114
<211> LENGTH: 27
<212> TYPE: DNA
<213> ORGANISM: Artificial Sequence
<220> FEATURE:
<223> OTHER INFORMATION: Primer impE2 64-A 1R

<400> SEQUENCE: 114
gaaaatcatc tgagccaaag agctcat        27

<210> SEQ ID NO 115
<211> LENGTH: 27
<212> TYPE: DNA
<213> ORGANISM: Artificial Sequence
<220> FEATURE:
<223> OTHER INFORMATION: Primer impE2 64-V 1R

<400> SEQUENCE: 115
gaaaatcatc tggaccaaag agctcat        27

<210> SEQ ID NO 116
<211> LENGTH: 27
<212> TYPE: DNA
<213> ORGANISM: Artificial Sequence
<220> FEATURE:
<223> OTHER INFORMATION: Primer impE2 64-I 1R

<400> SEQUENCE: 116
gaaaatcatc tggatcaaag agctcat        27

<210> SEQ ID NO 117
<211> LENGTH: 27
<212> TYPE: DNA
<213> ORGANISM: Artificial Sequence
<220> FEATURE:
<223> OTHER INFORMATION: Primer impE2 64-L 1R

<400> SEQUENCE: 117
gaaaatcatc tgcagcaaag agctcat        27

<210> SEQ ID NO 118
<211> LENGTH: 27
<212> TYPE: DNA
<213> ORGANISM: Artificial Sequence
<220> FEATURE:
<223> OTHER INFORMATION: Primer impE2 64-M 1R

<400> SEQUENCE: 118
gaaaatcatc tgcatcaaag agctcat        27

<210> SEQ ID NO 119
<211> LENGTH: 27
<212> TYPE: DNA
<213> ORGANISM: Artificial Sequence
<220> FEATURE:
<223> OTHER INFORMATION: Primer impE2 64-F 1R

<400> SEQUENCE: 119
gaaaatcatc tggaacaaag agctcat                27

<210> SEQ ID NO 120
<211> LENGTH: 27
<212> TYPE: DNA
<213> ORGANISM: Artificial Sequence
<220> FEATURE:
<223> OTHER INFORMATION: Primer impE2 64-Y 1R

<400> SEQUENCE: 120
gaaaatcatc tggtacaaag agctcat                27

<210> SEQ ID NO 121
<211> LENGTH: 27
<212> TYPE: DNA
<213> ORGANISM: Artificial Sequence
<220> FEATURE:
<223> OTHER INFORMATION: Primer impE2 64-W 1R

<400> SEQUENCE: 121
gaaaatcatc tgccacaaag agctcat                27

<210> SEQ ID NO 122
<211> LENGTH: 30
<212> TYPE: DNA
<213> ORGANISM: Artificial Sequence
<220> FEATURE:
<223> OTHER INFORMATION: Primer XbaI-impE2 64 2R

<400> SEQUENCE: 122
gggtctagac ggtcaatgaa gtctcaacgg             30

<210> SEQ ID NO 123
<211> LENGTH: 27
<212> TYPE: DNA
<213> ORGANISM: Artificial Sequence
<220> FEATURE:
<223> OTHER INFORMATION: Primer impE2 64-R 2F

<400> SEQUENCE: 123
atgagctctt tgcgccagat gattttc                27

<210> SEQ ID NO 124
<211> LENGTH: 27
<212> TYPE: DNA
<213> ORGANISM: Artificial Sequence
<220> FEATURE:
<223> OTHER INFORMATION: Primer impE2 64-H 2F

<400> SEQUENCE: 124
atgagctctt tgcaccagat gattttc                27

<210> SEQ ID NO 125
<211> LENGTH: 27
<212> TYPE: DNA
<213> ORGANISM: Artificial Sequence
<220> FEATURE:
<223> OTHER INFORMATION: Primer impE2 64-D 2F

```
<400> SEQUENCE: 125
atgagctctt tggaccagat gattttc                                              27

<210> SEQ ID NO 126
<211> LENGTH: 27
<212> TYPE: DNA
<213> ORGANISM: Artificial Sequence
<220> FEATURE:
<223> OTHER INFORMATION: Primer impE2 64-K 2F

<400> SEQUENCE: 126
atgagctctt tgaagcagat gattttc                                              27

<210> SEQ ID NO 127
<211> LENGTH: 27
<212> TYPE: DNA
<213> ORGANISM: Artificial Sequence
<220> FEATURE:
<223> OTHER INFORMATION: Primer impE2 64-S 2F

<400> SEQUENCE: 127
atgagctctt tgtcccagat gattttc                                              27

<210> SEQ ID NO 128
<211> LENGTH: 27
<212> TYPE: DNA
<213> ORGANISM: Artificial Sequence
<220> FEATURE:
<223> OTHER INFORMATION: Primer impE2 64-T 2F

<400> SEQUENCE: 128
atgagctctt tgacccagat gattttc                                              27

<210> SEQ ID NO 129
<211> LENGTH: 27
<212> TYPE: DNA
<213> ORGANISM: Artificial Sequence
<220> FEATURE:
<223> OTHER INFORMATION: Primer impE2 64-N 2F

<400> SEQUENCE: 129
atgagctctt tgaaccagat gattttc                                              27

<210> SEQ ID NO 130
<211> LENGTH: 27
<212> TYPE: DNA
<213> ORGANISM: Artificial Sequence
<220> FEATURE:
<223> OTHER INFORMATION: Primer impE2 64-Q 2F

<400> SEQUENCE: 130
atgagctctt tgcagcagat gattttc                                              27

<210> SEQ ID NO 131
<211> LENGTH: 27
<212> TYPE: DNA
<213> ORGANISM: Artificial Sequence
<220> FEATURE:
<223> OTHER INFORMATION: Primer impE2 64-C 2F

<400> SEQUENCE: 131
atgagctctt tgtgccagat gattttc                                              27

<210> SEQ ID NO 132
```

<211> LENGTH: 27
<212> TYPE: DNA
<213> ORGANISM: Artificial Sequence
<220> FEATURE:
<223> OTHER INFORMATION: Primer impE2 64-P 2F

<400> SEQUENCE: 132
atgagctctt tgccacagat gattttc                                27

<210> SEQ ID NO 133
<211> LENGTH: 27
<212> TYPE: DNA
<213> ORGANISM: Artificial Sequence
<220> FEATURE:
<223> OTHER INFORMATION: Primer impE2 64-A 2F

<400> SEQUENCE: 133
atgagctctt tggctcagat gattttc                                27

<210> SEQ ID NO 134
<211> LENGTH: 27
<212> TYPE: DNA
<213> ORGANISM: Artificial Sequence
<220> FEATURE:
<223> OTHER INFORMATION: Primer impE2 64-V 2F

<400> SEQUENCE: 134
atgagctctt tggtccagat gattttc                                27

<210> SEQ ID NO 135
<211> LENGTH: 27
<212> TYPE: DNA
<213> ORGANISM: Artificial Sequence
<220> FEATURE:
<223> OTHER INFORMATION: Primer impE2 64-I 2F

<400> SEQUENCE: 135
atgagctctt tgatccagat gattttc                                27

<210> SEQ ID NO 136
<211> LENGTH: 27
<212> TYPE: DNA
<213> ORGANISM: Artificial Sequence
<220> FEATURE:
<223> OTHER INFORMATION: Primer impE2 64-L 2F

<400> SEQUENCE: 136
atgagctctt tgctgcagat gattttc                                27

<210> SEQ ID NO 137
<211> LENGTH: 27
<212> TYPE: DNA
<213> ORGANISM: Artificial Sequence
<220> FEATURE:
<223> OTHER INFORMATION: Primer impE2 64-M 2F

<400> SEQUENCE: 137
atgagctctt tgatgcagat gattttc                                27

<210> SEQ ID NO 138
<211> LENGTH: 27
<212> TYPE: DNA
<213> ORGANISM: Artificial Sequence
<220> FEATURE:
<223> OTHER INFORMATION: Primer impE2 64-F 2F

<400> SEQUENCE: 138

```
atgagctctt tgttccagat gattttc                                        27
```

<210> SEQ ID NO 139
<211> LENGTH: 27
<212> TYPE: DNA
<213> ORGANISM: Artificial Sequence
<220> FEATURE:
<223> OTHER INFORMATION: Primer impE2 64-Y 2F

<400> SEQUENCE: 139

```
atgagctctt tgtaccagat gattttc                                        27
```

<210> SEQ ID NO 140
<211> LENGTH: 27
<212> TYPE: DNA
<213> ORGANISM: Artificial Sequence
<220> FEATURE:
<223> OTHER INFORMATION: Primer impE2 64-W 2F

<400> SEQUENCE: 140

```
atgagctctt tgtggcagat gattttc                                        27
```

<210> SEQ ID NO 141
<211> LENGTH: 221
<212> TYPE: PRT
<213> ORGANISM: unknown
<220> FEATURE:
<223> OTHER INFORMATION: ImpE1-CJI0323

<400> SEQUENCE: 141

Leu His Ala Val Gln Glu Val Asn Asp Asn Glu Glu Asp Ser Leu Pro
1               5                   10                  15

Gly Ser Asp Leu Gly Leu Arg Glu Gln Lys Arg Leu Ala Thr Lys His
            20                  25                  30

Arg Ile Glu Asp Ala Ala Thr Arg Leu Val Asp Glu Ser Ser Phe Asp
        35                  40                  45

Lys Val Thr Ile Glu Glu Ile Cys Glu Ala Ala Gly Ile Ser Arg Arg
    50                  55                  60

Thr Phe Phe Asn Tyr Phe Ser Thr Lys Glu Ser Ala Val Ile Gly Ala
65                  70                  75                  80

Ser Ser Glu Pro Leu Thr Glu Lys Gln Arg Asn Asp Phe Leu Asn Ala
                85                  90                  95

Asp Ala Ser Asn Leu Leu Gln Leu Met Val Glu Gln Ile Lys Gln His
            100                 105                 110

Leu Glu Ser Ser His Gln Ser Gln Ala Ile His Asp Arg Arg Gln Arg
        115                 120                 125

Ile Phe Ala Asp Pro Asp Val Ala Val Arg Ala Met Ala Phe Arg Lys
    130                 135                 140

Glu Arg Ser Arg Glu Thr Met Glu Leu Ile Ala Gln Arg Leu Arg Glu
145                 150                 155                 160

His Pro Glu Lys Gln Arg Ala Pro Glu Leu Asp Pro Glu Thr Glu Ala
                165                 170                 175

Met Leu Leu Ser Gly Phe Ile Arg Glu Ala Thr Trp Met Ala Ile Ser
            180                 185                 190

Arg Pro Asp Arg Asp Cys Ala Leu Pro Val Gly Asp Arg Ile Tyr Arg
        195                 200                 205

Ala Met Glu Leu Val Lys Asn Tyr Thr Lys Gly Leu Glu
    210                 215                 220

<210> SEQ ID NO 142
<211> LENGTH: 549
<212> TYPE: PRT
<213> ORGANISM: unknown
<220> FEATURE:
<223> OTHER INFORMATION: ImpE2-CJI0323

<400> SEQUENCE: 142

Met Ile Ala Lys Asn Ser Thr Pro Ser Thr Ala Gly His Ala Ser Ala
1               5                   10                  15

His Thr Ala Glu Glu Phe Pro Val Ala Asn Ala Glu Met Ala Thr Pro
            20                  25                  30

Ser Ala Ile Asp Pro Asn His Gly Lys Lys Thr Ala Asp Asn Val Gly
        35                  40                  45

Ile Ile Phe Ala Ala Leu Met Leu Thr Met Leu Met Ser Ser Leu Glu
    50                  55                  60

Gln Met Ile Phe Gly Ser Ala Leu Pro Thr Ile Val Gly Glu Leu Gly
65                  70                  75                  80

Gly Val Asp Gln Met Ser Trp Val Ile Ser Ala Phe Met Val Thr Met
                85                  90                  95

Thr Ile Ala Met Pro Leu Ala Gly Gln Leu Gly Asp Arg Met Gly Arg
            100                 105                 110

Lys Trp Val Tyr Ile Ser Gly Ile Ser Ile Phe Val Ile Gly Ser Thr
        115                 120                 125

Leu Gly Gly Phe Ala Asn Gly Met Gly Met Leu Ile Thr Gly Arg Ala
    130                 135                 140

Ile Gln Gly Phe Gly Ala Gly Ile Met Met Ile Ser Ser Gln Ser Ile
145                 150                 155                 160

Val Ala Glu Val Val Ser Ala Arg Glu Arg Gly Lys Phe Met Gly Ile
                165                 170                 175

Met Gly Gly Val Phe Gly Val Ser Ser Val Leu Gly Pro Val Leu Gly
            180                 185                 190

Gly Trp Phe Thr Asp Gly Pro Gly Trp Arg Trp Gly Leu Trp Ile Asn
        195                 200                 205

Ile Pro Leu Gly Leu Leu Ala Ile Ile Val Cys Ala Phe Val Leu Lys
    210                 215                 220

Leu Arg Val Gly Glu Gln Gly Phe Lys Gly Phe Asp Trp Met Gly Phe
225                 230                 235                 240

Ala Ala Ile Ala Ile Thr Thr Ser Thr Leu Ile Leu Leu Thr Thr Trp
                245                 250                 255

Gly Gly Ser Glu Tyr Glu Trp Thr Ser Pro Thr Ile Leu Ser Met Ala
            260                 265                 270

Ala Val Val Ile Val Gly Ala Leu Leu Thr Val Phe Ile Glu Ser Arg
        275                 280                 285

Ala Ser Gln Pro Leu Ile Pro Val Gln Leu Phe Lys Asn Arg Asn Met
    290                 295                 300

Val Leu Thr Thr Leu Ala Gly Thr Val Leu Gly Leu Ala Met Met Gly
305                 310                 315                 320

Val Leu Gly Tyr Met Pro Thr Tyr Leu Gln Met Val His Thr Leu Thr
                325                 330                 335

Pro Thr Glu Ala Gly Leu Met Met Ile Pro Met Met Val Gly Met Ile
            340                 345                 350

Gly Val Ser Thr Gly Val Gly Phe Ile Ile Ala Lys Thr Gly Asn Tyr
        355                 360                 365

Lys Tyr Tyr Pro Ile Ala Gly Leu Ala Ile Thr Ala Phe Ala Leu Trp
    370                 375                 380

Trp Met Ser Gln Met Thr Val Glu Thr Ser Leu Thr Gly Ile Gly Val
385                 390                 395                 400

Arg Phe Leu Val Phe Gly Val Gly Leu Gly Phe Val Met Gln Val Leu
                405                 410                 415

Val Leu Ile Val Gln Asn Ser Phe Pro Val Ser Gln Val Gly Thr Ala
                420                 425                 430

Thr Ala Ala Asn Asn Phe Phe Arg Gln Ile Gly Ser Ala Leu Gly Ala
            435                 440                 445

Ser Ile Val Gly Ser Met Phe Ile His Asn Met Gln Asn Glu Met Ala
    450                 455                 460

Thr Arg Leu Pro Asp Ala Leu Ala Ser Leu Gly Lys Glu Gly Ala Ala
465                 470                 475                 480

Ile Ser Gln Gln Phe Gln Gly Ala Asp Ala Ala Asn Ser Leu Thr Pro
                485                 490                 495

His Ala Val Ala Glu Leu Pro Asp Val Leu Arg Asp Ala Ile Leu Asn
            500                 505                 510

Ser Tyr Asn Asp Gly Leu Thr Pro Val Ile Gly Met Met Val Pro Leu
    515                 520                 525

Ala Ile Val Ala Met Leu Ile Leu Phe Pro Leu Arg Gln Glu Arg Leu
530                 535                 540

Lys Glu Thr Ile Glu
545

<210> SEQ ID NO 143
<211> LENGTH: 669
<212> TYPE: DNA
<213> ORGANISM: unknown
<220> FEATURE:
<223> OTHER INFORMATION: ImpE1 NT - CJI0323

<400> SEQUENCE: 143
ttgcatgctg tgcaagaagt taatgacaat gaagaagact ccctccctgg cagtgacctc      60
gggttaaggg agcagaagcg attggcaacc aagcatcgca tcgaagacgc cgcgacacgg     120
ttggttgatg aatcgagctt tgacaaagta acaattgaag aaatttgcga agccgccggg     180
atttcccgac gcaccttttt taattatttc agcacgaaag aaagcgccgt tattggcgcg     240
tcctcggaac cgttgacgga aaagcaacgc aatgacttct gaatgctga cgccagcaat     300
ctcctgcagc tgatggttga gcagatcaaa caacacttgg agtcttctca ccagagtcaa     360
gcgattcacg accgtcgtca gcgaatcttt gcggatccgg atgtcgcggt acgtgcaatg     420
gcgtttcgca aggaacgctc acgggaaacc atggagctaa tcgctcaacg tcttcgggag     480
catcctgaaa acaacgcgc cccagaattg gatccggaaa cagaggcgat gctgctgagc     540
ggattcattc gcgaagccac ctggatggct atctcacgac ccgatcgtga ttgtgcactg     600
ccagtgggtg accgcatcta tcgcgcgatg gaattggtaa agaattacac gaaaggactg     660
gaatgatag                                                            669

<210> SEQ ID NO 144
<211> LENGTH: 1650
<212> TYPE: DNA
<213> ORGANISM: Unknown
<220> FEATURE:
<223> OTHER INFORMATION: ImpE2 NT - CJI0323

<400> SEQUENCE: 144

-continued

```
atgatagcta aaaactccac cccaagcacg gccggccacg ccagtgctca cactgcggaa      60
gaattcccag tggccaatgc tgaaatggca acgccttcag caatcgaccc aaaccacggt     120
aaaaagaccg cggataacgt cggcattatc ttcgctgcct tgatgctcac catgctgatg     180
agctctttgg agcagatgat tttcggttcc gctctgccaa ccatcgtcgg cgagctcggc     240
ggcgtggacc agatgagctg gtaatttca gcatttatgg tcaccatgac cattgctatg      300
ccactagccg tcagctcgg tgaccgcatg gccgcaagt gggtctacat ctcaggtatc       360
tccattttcg ttattggctc gacgctcggt ggctttgcca atggcatggg catgctgatc    420
accggacgtg caatccaggg cttcggtgcc ggcatcatga tgatttcctc gcagtcgatt     480
gtggctgagg ttgtctccgc acgtgagcgc ggcaagttca tgggtattat gggcggcgtc    540
tttggcgtct cctccgtact gggtccagtt ctcggtggct ggttcaccga tggtcccggt    600
tggcgttggg gcctgtggat caacattcca ctgggtctgc tggcaattat tgtctgcgct    660
ttcgtactga agctgcgcgt gggcgagcaa ggctttaagg gctttgactg gatgggtttt   720
gcggccatcg caatcacgac cagcacccctg attctgctca ccacttgggg cggaagcgaa  780
tacgagtgga cttccccaac tattttgtcc atggctgccg tagtcatcgt cggcgcgctg   840
ctcaccgtgt tcattgagtc gcgtgcatcc cagccgctga tcccggttca gctatttaag  900
aaccgcaaca tggttttgac caccctcgcc ggtactgttt tgggtctggc catgatgggc  960
gtgctcggct acatgccaac ctacctgcag atggtgcaca ccctgacgcc aactgaagca 1020
ggcttgatga tgatcccgat gatggtcggc atgatcggtg tctccactgg tgttggcttc 1080
atcatcgcta agaccggcaa ctacaagtac tacccatcg cgggcctggc catcacggcg   1140
tttgcttgt ggtggatgtc ccagatgacc gttgagactt cattgaccgg tatcggagtt   1200
cgcttccttg tattcggtgt cggcttgggc tttgtcatgc aggtactggt gctgattgtt  1260
caaaactcct ccctgtatc gcaggtcggt actgccacgg cggctaataa cttcttccgc   1320
cagattggtt cggcattggg tgcttccatc gtgggttcga tgttcattca caatatgcag  1380
aatgagatgg ctacccgttt gcctgatgcc cttgcatcgt tgggcaagga aggcgccgct  1440
atttcgcagc agttccaagg tgcagatgcc gccaactcct tgactccgca cgcagtcgca  1500
gagcttcccg atgtcctccg tgacgctatc ttaaattcct acaatgacgg tctgaccccc  1560
gtgattggca tgatggtgcc actggccatt gttgcaatgc tgattttgtt cccactgcgc  1620
caagagcgct tgaaggaaac catcgaataa                                    1650
```

<210> SEQ ID NO 145
<211> LENGTH: 222
<212> TYPE: PRT
<213> ORGANISM: Unknown
<220> FEATURE:
<223> OTHER INFORMATION: ImpE1-164K

<400> SEQUENCE: 145

Leu His Ala Val Gln Glu Val Asn Asp Asn Glu Asp Ser Leu Pro
1               5                   10                  15

Gly Ser Asp Leu Gly Leu Arg Glu Gln Lys Arg Leu Ala Thr Lys His
            20                  25                  30

Arg Ile Glu Asp Ala Ala Thr Arg Leu Val Asp Glu Ser Ser Phe Asp
        35                  40                  45

Lys Val Thr Ile Glu Glu Ile Cys Glu Ala Ala Gly Ile Ser Arg Arg
    50                  55                  60

```
Thr Phe Phe Asn Tyr Phe Ser Thr Lys Glu Ser Ala Val Ile Gly Ala
 65                  70                  75                  80

Ser Ser Glu Pro Leu Thr Glu Lys Gln Arg Asn Asp Phe Leu Asn Ala
                 85                  90                  95

Asp Ala Ser Asn Leu Leu Gln Leu Met Val Glu Gln Ile Lys Gln His
            100                 105                 110

Leu Glu Ser Ser His Gln Ser Gln Ala Ile His Asp Arg Arg Gln Arg
        115                 120                 125

Ile Phe Ala Asp Pro Asp Val Ala Val Arg Ala Met Ala Phe Arg Lys
130                 135                 140

Glu Arg Ser Arg Glu Thr Met Glu Leu Ile Ala Gln Arg Leu Arg Glu
145                 150                 155                 160

His Pro Glu Lys Gln Arg Ala Pro Glu Leu Asp Pro Glu Thr Glu Ala
                165                 170                 175

Met Leu Leu Ser Gly Phe Ile Arg Glu Ala Thr Trp Met Ala Ile Ser
            180                 185                 190

Arg Pro Asp Arg Asp Cys Ala Leu Pro Val Gly Asp Arg Ile Tyr Arg
        195                 200                 205

Ala Met Glu Leu Val Lys Asn Tyr Thr Lys Gly Leu Glu Trp
210                 215                 220
```

<210> SEQ ID NO 146
<211> LENGTH: 669
<212> TYPE: DNA
<213> ORGANISM: Unknown
<220> FEATURE:
<223> OTHER INFORMATION: ImpE1 NT-164K

<400> SEQUENCE: 146

```
ttgcatgctg tgcaagaagt taatgacaat gaagaagact ccctccctgg cagtgacctc      60
gggttaaggg agcagaagcg attggcaacc aagcatcgca tcgaagacgc cgcgacacgg     120
ttggttgatg aatcgagctt tgacaaagta acaattgaag aaatttgcga agccgccggg     180
atttcccgac gcaccttttt taattatttc agcacgaaag aaagcgccgt tattggcgcg     240
tcctcggaac cgttgacgga aaagcaacgc aatgacttct tgaatgctga cgccagcaat     300
ctcctgcagc tgatggttga gcagatcaaa caacacttgg agtcttctca ccagagtcaa     360
gcgattcacg accgtcgtca gcgaatcttt gcggatccgg atgtcgcggt acgtgcaatg     420
gcgtttcgca aggaacgctc acgggaaacc atggagctaa tcgctcaacg tcttcgggag     480
catcctgaaa acaacgcgc cccagaattg atccggaaa cagaggcgat gctgctgagc     540
ggattcattc gcgaagccac ctggatggct atctcacgac ccgatcgtga ttgtgcactg     600
ccagtgggtg accgcatcta tcgcgcgatg gaattggtaa agaattacac gaaaggactg     660
gaatggtag                                                            669
```

<210> SEQ ID NO 147
<211> LENGTH: 549
<212> TYPE: PRT
<213> ORGANISM: Unknown
<220> FEATURE:
<223> OTHER INFORMATION: ImpE2 - V2I

<400> SEQUENCE: 147

```
Met Ile Ala Lys Asn Ser Thr Pro Ser Thr Ala Gly His Ala Ser Ala
1               5                   10                  15

His Thr Ala Glu Glu Phe Pro Val Ala Asn Ala Glu Met Ala Thr Pro
            20                  25                  30
```

```
Ser Ala Ile Asp Pro Asn His Gly Lys Lys Thr Ala Asp Asn Val Gly
         35                  40                  45

Ile Ile Phe Ala Ala Leu Met Leu Thr Met Leu Met Ser Ser Leu Gly
 50                  55                  60

Gln Met Ile Phe Gly Ser Ala Leu Pro Thr Ile Val Gly Glu Leu Gly
 65                  70                  75                  80

Gly Val Asp Gln Met Ser Trp Val Ile Ser Ala Phe Met Val Thr Met
                 85                  90                  95

Thr Ile Ala Met Pro Leu Ala Gly Gln Leu Gly Asp Arg Met Gly Arg
                100                 105                 110

Lys Trp Val Tyr Ile Ser Gly Ile Ser Ile Phe Val Ile Gly Ser Thr
                115                 120                 125

Leu Gly Gly Phe Ala Asn Gly Met Gly Met Leu Ile Thr Gly Arg Ala
        130                 135                 140

Ile Gln Gly Phe Gly Ala Gly Ile Met Met Ile Ser Ser Gln Ser Ile
145                 150                 155                 160

Val Ala Glu Val Val Ser Ala Arg Glu Arg Gly Lys Phe Met Gly Ile
                165                 170                 175

Met Gly Gly Val Phe Gly Val Ser Ser Val Leu Gly Pro Val Leu Gly
        180                 185                 190

Gly Trp Phe Thr Asp Gly Pro Gly Trp Arg Trp Gly Leu Trp Ile Asn
        195                 200                 205

Ile Pro Leu Gly Leu Leu Ala Ile Ile Val Cys Ala Phe Val Leu Lys
        210                 215                 220

Leu Arg Val Gly Glu Gln Gly Phe Lys Gly Phe Asp Trp Met Gly Phe
225                 230                 235                 240

Ala Ala Ile Ala Ile Thr Thr Ser Thr Leu Ile Leu Leu Thr Thr Trp
                245                 250                 255

Gly Gly Ser Glu Tyr Glu Trp Thr Ser Pro Thr Ile Leu Ser Met Ala
        260                 265                 270

Ala Val Val Ile Val Gly Ala Leu Leu Thr Val Phe Ile Glu Ser Arg
        275                 280                 285

Ala Ser Gln Pro Leu Ile Pro Val Gln Leu Phe Lys Asn Arg Asn Met
        290                 295                 300

Val Leu Thr Thr Leu Ala Gly Thr Val Leu Gly Leu Ala Met Met Gly
305                 310                 315                 320

Val Leu Gly Tyr Met Pro Thr Tyr Leu Gln Met Val His Thr Leu Thr
                325                 330                 335

Pro Thr Glu Ala Gly Leu Met Met Ile Pro Met Met Val Gly Met Ile
        340                 345                 350

Gly Val Ser Thr Gly Val Gly Phe Ile Ile Ala Lys Thr Gly Asn Tyr
        355                 360                 365

Lys Tyr Tyr Pro Ile Ala Gly Leu Ala Ile Thr Ala Phe Ala Leu Trp
        370                 375                 380

Trp Met Ser Gln Met Thr Val Glu Thr Ser Leu Thr Gly Ile Gly Val
385                 390                 395                 400

Arg Phe Leu Val Phe Gly Val Gly Leu Gly Phe Val Met Gln Val Leu
                405                 410                 415

Val Leu Ile Val Gln Asn Ser Phe Pro Val Ser Gln Val Gly Thr Ala
        420                 425                 430

Thr Ala Ala Asn Asn Phe Phe Arg Gln Ile Gly Ser Ala Leu Gly Ala
        435                 440                 445
```

Ser Ile Val Gly Ser Met Phe Ile His Asn Met Gln Asn Glu Met Ala
            450                 455                 460

Thr Arg Leu Pro Asp Ala Leu Ala Ser Leu Gly Lys Glu Gly Ala Ala
465                 470                 475                 480

Ile Ser Gln Gln Phe Gln Gly Ala Asp Ala Ala Asn Ser Leu Thr Pro
                485                 490                 495

His Ala Val Ala Glu Leu Pro Asp Val Leu Arg Asp Ala Ile Leu Asn
            500                 505                 510

Ser Tyr Asn Asp Gly Leu Thr Pro Val Ile Gly Met Met Val Pro Leu
        515                 520                 525

Ala Ile Val Ala Met Leu Ile Leu Phe Pro Leu Arg Gln Glu Arg Leu
    530                 535                 540

Lys Glu Thr Ile Glu
545

<210> SEQ ID NO 148
<211> LENGTH: 1650
<212> TYPE: DNA
<213> ORGANISM: Unknown
<220> FEATURE:
<223> OTHER INFORMATION: ImpE2 NT - V2I

<400> SEQUENCE: 148

```
atgatagcta aaaactccac cccaagcacg gccggccacg ccagtgctca cactgcggaa      60
gaattcccag tggccaatgc tgaaatggca acgccttcag caatcgaccc aaaccacggt     120
aaaaagaccg cggataacgt cggcattatc ttcgctgcct tgatgctcac catgctgatg     180
agctctttgg ggcagatgat tttcggttcc gctctgccaa ccatcgtcgg cgagctcggc     240
ggcgtggacc agatgagctg gtaatttca gcatttatgg tcaccatgac cattgctatg     300
ccactagccg gtcagctcgg tgaccgcatg ggccgcaagt gggtctacat ctcaggtatc     360
tccattttcg ttattggctc gacgctcggt ggctttgcca atggcatggg catgctgatc     420
accggacgtg caatccaggg cttcggtgcc ggcatcatga tgatttcctc gcagtcgatt     480
gtggctgagg ttgtctccgc acgtgagcgc ggcaagttca tgggtattat gggcggcgtc     540
tttggcgtct cctccgtact gggtccagtt ctcgtggct ggttcaccga tggtcccggt     600
tggcgttggg gcctgtggat caacattcca ctgggtctgc tggcaattat tgtctgcgct     660
ttcgtactga agctgcgcgt gggcgagcaa ggctttaagg ctttgactg gatgggtttt     720 gcggccatcg caatcacgac cagcacccctg attctgctca ccacttgggg cggaagcgaa     780
tacgagtgga cttccccaac tatttttgtcc atggctgccg tagtcatcgt cggcgcgctg     840
ctcaccgtgt tcattgagtc gcgtgcatcc cagccgctga tcccggttca gctatttaag     900
aaccgcaaca tggttttgac caccctcgcc ggtactgttt gggtctggc catgatgggc     960 gtgctcggct acatgccaac ctacctgcag atggtgcaca ccctgacgcc aactgaagca    1020
ggcttgatga tgatcccgat gatggtcggc atgatcggtg tctccactgg tgttggcttc    1080
atcatcgcta agaccggcaa ctacaagtac tacccatcg cgggcctggc catcacggcg    1140 tttgcttttgt ggtggatgtc ccagatgacc gttgagactt cattgaccgg tatcggagtt    1200
cgcttccttg tattcggtgt cggcttgggc tttgtcatgc aggtactggt gctgattgtt    1260
caaaactcct tccctgtatc gcaggtcggt actgccacgg cggctaataa cttcttccgc    1320
cagattggtt cggcattggg tgcttccatc gtgggttcga tgttcattca caatatgcag    1380
aatgagatgg ctaccgtttt gcctgatgcc cttgcatcgt tgggcaagga aggcgccgct    1440
```

```
atttcgcagc agttccaagg tgcagatgcc gccaactcct tgactccgca cgcagtcgca    1500
gagcttcccg atgtcctccg tgacgctatc ttaaattcct acaatgacgg tctgaccccc    1560
gtgattggca tgatggtgcc actggccatt gttgcaatgc tgattttgtt cccactgcgc    1620
caagagcgct tgaaggaaac catcgaataa                                      1650
```

<210> SEQ ID NO 149
<211> LENGTH: 549
<212> TYPE: PRT
<213> ORGANISM: Unknown
<220> FEATURE:
<223> OTHER INFORMATION: ImpE2 - G64E

<400> SEQUENCE: 149

```
Met Val Ala Lys Asn Ser Thr Pro Ser Thr Ala Gly His Ala Ser Ala
1               5                   10                  15

His Thr Ala Glu Glu Phe Pro Val Ala Asn Ala Glu Met Ala Thr Pro
                20                  25                  30

Ser Ala Ile Asp Pro Asn His Gly Lys Lys Thr Ala Asp Asn Val Gly
            35                  40                  45

Ile Ile Phe Ala Ala Leu Met Leu Thr Met Leu Met Ser Ser Leu Glu
        50                  55                  60

Gln Met Ile Phe Gly Ser Ala Leu Pro Thr Ile Val Gly Glu Leu Gly
65                  70                  75                  80

Gly Val Asp Gln Met Ser Trp Val Ile Ser Ala Phe Met Val Thr Met
                85                  90                  95

Thr Ile Ala Met Pro Leu Ala Gly Gln Leu Gly Asp Arg Met Gly Arg
            100                 105                 110

Lys Trp Val Tyr Ile Ser Gly Ile Ser Ile Phe Val Ile Gly Ser Thr
        115                 120                 125

Leu Gly Gly Phe Ala Asn Gly Met Gly Met Leu Ile Thr Gly Arg Ala
    130                 135                 140

Ile Gln Gly Phe Gly Ala Gly Ile Met Met Ile Ser Ser Gln Ser Ile
145                 150                 155                 160

Val Ala Glu Val Val Ser Ala Arg Glu Arg Gly Lys Phe Met Gly Ile
                165                 170                 175

Met Gly Gly Val Phe Gly Val Ser Ser Val Leu Gly Pro Val Leu Gly
            180                 185                 190

Gly Trp Phe Thr Asp Gly Pro Gly Trp Arg Trp Gly Leu Trp Ile Asn
        195                 200                 205

Ile Pro Leu Gly Leu Leu Ala Ile Ile Val Cys Ala Phe Val Leu Lys
    210                 215                 220

Leu Arg Val Gly Glu Gln Gly Phe Lys Gly Phe Asp Trp Met Gly Phe
225                 230                 235                 240

Ala Ala Ile Ala Ile Thr Thr Ser Thr Leu Ile Leu Leu Thr Thr Trp
                245                 250                 255

Gly Gly Ser Glu Tyr Glu Trp Thr Ser Pro Thr Ile Leu Ser Met Ala
            260                 265                 270

Ala Val Val Ile Val Gly Ala Leu Leu Thr Val Phe Ile Glu Ser Arg
        275                 280                 285

Ala Ser Gln Pro Leu Ile Pro Val Gln Leu Phe Lys Asn Arg Asn Met
    290                 295                 300

Val Leu Thr Thr Leu Ala Gly Thr Val Leu Gly Leu Ala Met Met Gly
305                 310                 315                 320

Val Leu Gly Tyr Met Pro Thr Tyr Leu Gln Met Val His Thr Leu Thr
```

```
                325                 330                 335
Pro Thr Glu Ala Gly Leu Met Met Ile Pro Met Met Val Gly Met Ile
            340                 345                 350
Gly Val Ser Thr Gly Val Gly Phe Ile Ile Ala Lys Thr Gly Asn Tyr
            355                 360                 365
Lys Tyr Tyr Pro Ile Ala Gly Leu Ala Ile Thr Ala Phe Ala Leu Trp
            370                 375                 380
Trp Met Ser Gln Met Thr Val Glu Thr Ser Leu Thr Gly Ile Gly Val
385                 390                 395                 400
Arg Phe Leu Val Phe Gly Val Gly Leu Gly Phe Val Met Gln Val Leu
                405                 410                 415
Val Leu Ile Val Gln Asn Ser Phe Pro Val Ser Gln Val Gly Thr Ala
            420                 425                 430
Thr Ala Ala Asn Asn Phe Phe Arg Gln Ile Gly Ser Ala Leu Gly Ala
            435                 440                 445
Ser Ile Val Gly Ser Met Phe Ile His Asn Met Gln Asn Glu Met Ala
            450                 455                 460
Thr Arg Leu Pro Asp Ala Leu Ala Ser Leu Gly Lys Glu Gly Ala Ala
465                 470                 475                 480
Ile Ser Gln Gln Phe Gln Gly Ala Asp Ala Ala Asn Ser Leu Thr Pro
                485                 490                 495
His Ala Val Ala Glu Leu Pro Asp Val Leu Arg Asp Ala Ile Leu Asn
            500                 505                 510
Ser Tyr Asn Asp Gly Leu Thr Pro Val Ile Gly Met Met Val Pro Leu
            515                 520                 525
Ala Ile Val Ala Met Leu Ile Leu Phe Pro Leu Arg Gln Glu Arg Leu
            530                 535                 540
Lys Glu Thr Ile Glu
545

<210> SEQ ID NO 150
<211> LENGTH: 1650
<212> TYPE: DNA
<213> ORGANISM: Unknown
<220> FEATURE:
<223> OTHER INFORMATION: ImpE2 NT - G64E

<400> SEQUENCE: 150
atggtagcta aaaactccac cccaagcacg gccggccacg ccagtgctca cactgcggaa    60
gaattcccag tggccaatgc tgaaatggca acgccttcag caatcgaccc aaaccacggt   120
aaaaagaccg cggataacgt cggcattatc ttcgctgcct tgatgctcac catgctgatg   180
agctctttgg agcagatgat tttcggttcc gctctgccaa ccatcgtcgg cgagctcggc   240
ggcgtggacc agatgagctg gtaatttca gcatttatgg tcaccatgac cattgctatg   300
ccactagccg tcagctcgg tgaccgcatg ggccgcaagt gggtctacat ctcaggtatc   360
tccattttcg ttattggctc gacgctcggt ggctttgcca atggcatggg catgctgatc   420
accggacgtg caatccaggg cttcggtgcc ggcatcatga tgatttcctc gcagtcgatt   480
gtggctgagg ttgtctccgc acgtgagcgc ggcaagttca tgggtattat gggcggcgtc   540
tttggcgtct cctccgtact gggtccagtt ctcggtggct ggttcaccga tggtcccggt   600
tggcgttggg gcctgtggat caacattcca ctgggtctgc tggcaattat tgtctgcgct   660
ttcgtactga agctgcgcgt gggcgagcaa ggctttaagg ctttgactg gatgggtttt   720
gcggccatcg caatcacgac cagcacccctg attctgctca ccacttgggg cggaagcgaa   780
```

```
tacgagtgga cttccccaac tattttgtcc atggctgccg tagtcatcgt cggcgcgctg      840
ctcaccgtgt tcattgagtc gcgtgcatcc cagccgctga tcccggttca gctatttaag      900
aaccgcaaca tggttttgac caccctcgcc ggtactgttt tgggtctggc catgatgggc      960
gtgctcggct acatgccaac ctacctgcag atggtgcaca ccctgacgcc aactgaagca     1020
ggcttgatga tgatcccgat gatggtcggc atgatcggtg tctccactgg tgttggcttc     1080
atcatcgcta agaccggcaa ctacaagtac taccccatcg cgggcctggc catcacggcg     1140
tttgctttgt ggtggatgtc ccagatgacc gttgagactt cattgaccgg tatcggagtt     1200
cgcttccttg tattcggtgt cggcttgggc tttgtcatgc aggtactggt gctgattgtt     1260
caaaactcct tccctgtatc gcaggtcggt actgccacgg cggctaataa cttcttccgc     1320
cagattggtt cggcattggg tgcttccatc gtgggttcga tgttcattca caatatgcag     1380
aatgagatgg ctaccgtttt gcctgatgcc cttgcatcgt tgggcaagga aggcgccgct     1440
atttcgcagc agttccaagg tgcagatgcc gccaactcct tgactccgca cgcagtcgca     1500
gagcttcccg atgtcctccg tgacgctatc ttaaattcct acaatgacgg tctgaccccc     1560
gtgattggca tgatggtgcc actggccatt gttgcaatgc tgattttgtt cccactgcgc     1620
caagagcgct tgaaggaaac catcgaataa                                      1650

<210> SEQ ID NO 151
<211> LENGTH: 549
<212> TYPE: PRT
<213> ORGANISM: Unknown
<220> FEATURE:
<223> OTHER INFORMATION: ImpE2 - G64D

<400> SEQUENCE: 151

Met Val Ala Lys Asn Ser Thr Pro Ser Thr Ala Gly His Ala Ser Ala
1               5                   10                  15

His Thr Ala Glu Glu Phe Pro Val Ala Asn Ala Glu Met Ala Thr Pro
            20                  25                  30

Ser Ala Ile Asp Pro Asn His Gly Lys Lys Thr Ala Asp Asn Val Gly
        35                  40                  45

Ile Ile Phe Ala Ala Leu Met Leu Thr Met Leu Met Ser Ser Leu Asp
    50                  55                  60

Gln Met Ile Phe Gly Ser Ala Leu Pro Thr Ile Val Gly Glu Leu Gly
65                  70                  75                  80

Gly Val Asp Gln Met Ser Trp Val Ile Ser Ala Phe Met Val Thr Met
                85                  90                  95

Thr Ile Ala Met Pro Leu Ala Gly Gln Leu Gly Asp Arg Met Gly Arg
            100                 105                 110

Lys Trp Val Tyr Ile Ser Gly Ile Ser Ile Phe Val Ile Gly Ser Thr
        115                 120                 125

Leu Gly Gly Phe Ala Asn Gly Met Gly Met Leu Ile Thr Gly Arg Ala
    130                 135                 140

Ile Gln Gly Phe Gly Ala Gly Ile Met Met Ile Ser Ser Gln Ser Ile
145                 150                 155                 160

Val Ala Glu Val Val Ser Ala Arg Glu Arg Gly Lys Phe Met Gly Ile
                165                 170                 175

Met Gly Gly Val Phe Gly Val Ser Ser Val Leu Gly Pro Val Leu Gly
            180                 185                 190

Gly Trp Phe Thr Asp Gly Pro Gly Trp Arg Trp Gly Leu Trp Ile Asn
        195                 200                 205
```

```
Ile Pro Leu Gly Leu Leu Ala Ile Ile Val Cys Ala Phe Val Leu Lys
    210                 215                 220
Leu Arg Val Gly Glu Gln Gly Phe Lys Gly Phe Asp Trp Met Gly Phe
225                 230                 235                 240
Ala Ala Ile Ala Ile Thr Thr Ser Thr Leu Ile Leu Leu Thr Thr Trp
                245                 250                 255
Gly Gly Ser Glu Tyr Glu Trp Thr Ser Pro Thr Ile Leu Ser Met Ala
                260                 265                 270
Ala Val Val Ile Val Gly Ala Leu Leu Thr Val Phe Ile Glu Ser Arg
                275                 280                 285
Ala Ser Gln Pro Leu Ile Pro Val Gln Leu Phe Lys Asn Arg Asn Met
    290                 295                 300
Val Leu Thr Thr Leu Ala Gly Thr Val Leu Gly Leu Ala Met Met Gly
305                 310                 315                 320
Val Leu Gly Tyr Met Pro Thr Tyr Leu Gln Met Val His Thr Leu Thr
                325                 330                 335
Pro Thr Glu Ala Gly Leu Met Met Ile Pro Met Met Val Gly Met Ile
                340                 345                 350
Gly Val Ser Thr Gly Val Gly Phe Ile Ile Ala Lys Thr Gly Asn Tyr
                355                 360                 365
Lys Tyr Tyr Pro Ile Ala Gly Leu Ala Ile Thr Ala Phe Ala Leu Trp
    370                 375                 380
Trp Met Ser Gln Met Thr Val Glu Thr Ser Leu Thr Gly Ile Gly Val
385                 390                 395                 400
Arg Phe Leu Val Phe Gly Val Gly Leu Gly Phe Val Met Gln Val Leu
                405                 410                 415
Val Leu Ile Val Gln Asn Ser Phe Pro Val Ser Gln Val Gly Thr Ala
                420                 425                 430
Thr Ala Ala Asn Asn Phe Phe Arg Gln Ile Gly Ser Ala Leu Gly Ala
                435                 440                 445
Ser Ile Val Gly Ser Met Phe Ile His Asn Met Gln Asn Glu Met Ala
    450                 455                 460
Thr Arg Leu Pro Asp Ala Leu Ala Ser Leu Gly Lys Glu Gly Ala Ala
465                 470                 475                 480
Ile Ser Gln Gln Phe Gln Gly Ala Asp Ala Ala Asn Ser Leu Thr Pro
                485                 490                 495
His Ala Val Ala Glu Leu Pro Asp Val Leu Arg Asp Ala Ile Leu Asn
                500                 505                 510
Ser Tyr Asn Asp Gly Leu Thr Pro Val Ile Gly Met Met Val Pro Leu
    515                 520                 525
Ala Ile Val Ala Met Leu Ile Leu Phe Pro Leu Arg Gln Glu Arg Leu
530                 535                 540
Lys Glu Thr Ile Glu
545
```

<210> SEQ ID NO 152
<211> LENGTH: 1650
<212> TYPE: DNA
<213> ORGANISM: Unknown
<220> FEATURE:
<223> OTHER INFORMATION: ImpE2 NT - G64D

<400> SEQUENCE: 152
atggtagcta aaaactccac cccaagcacg gccggccacg ccagtgctca cactgcggaa    60

```
gaattcccag tggccaatgc tgaaatggca acgccttcag caatcgaccc aaaccacggt      120
aaaaagaccg cggataacgt cggcattatc ttcgctgcct tgatgctcac catgctgatg      180
agctctttgg accagatgat tttcggttcc gctctgccaa ccatcgtcgg cgagctcggc      240
ggcgtggacc agatgagctg gtaatttca gcatttatgg tcaccatgac cattgctatg       300
ccactagccg gtcagctcgg tgaccgcatg ggccgcaagt gggtctacat ctcaggtatc      360
tccattttcg ttattggctc gacgctcggt ggctttgcca atggcatggg catgctgatc      420
accggacgtg caatccaggg cttcggtgcc ggcatcatga tgatttcctc gcagtcgatt      480
gtggctgagg ttgtctccgc acgtgagcgc ggcaagttca tgggtattat gggcggcgtc      540
tttggcgtct cctccgtact gggtccagtt ctcggtggct ggttcaccga tggtcccggt      600
tggcgttggg gcctgtggat caacattcca ctgggtctgc tggcaattat tgtctgcgct      660
ttcgtactga agctgcgcgt gggcgagcaa ggctttaagg ctttgactg gatgggtttt       720 gcggccatcg caatcacgac cagcaccctg attctgctca ccacttgggg cggaagcgaa      780
tacgagtgga cttccccaac tattttgtcc atggctgccg tagtcatcgt cggcgcgctg      840
ctcaccgtgt tcattgagtc gcgtgcatcc cagccgctga tcccggttca gctatttaag      900
aaccgcaaca tggttttgac cacccctcgcc ggtactgttt gggtctggc catgatgggc      960 gtgctcggct acatgccaac ctacctgcag atggtgcaca ccctgacgcc aactgaagca      1020
ggcttgatga tgatcccgat gatggtcggc atgatcggtg tctccactgg tgttggcttc      1080
atcatcgcta agaccggcaa ctacaagtac taccccatcg cgggcctggc catcacggcg      1140 tttgcttttgt ggtggatgtc ccagatgacc gttgagactt cattgaccgg tatcggagtt      1200
cgcttccttg tattcggtgt cggcttgggc tttgtcatgc aggtactggt gctgattgtt      1260
caaaactcct tccctgtatc gcaggtcggt actgccacgg cggctaataa cttcttccgc      1320
cagattggtt cggcattggg tgcttccatc gtgggttcga tgttcattca caatatgcag      1380
aatgagatgg ctaccgcgttt gcctgatgcc cttgcatcgt tgggcaagga aggcgccgct      1440
atttcgcagc agttccaagg tgcagatgcc gccaactcct tgactccgca cgcagtcgca      1500
gagcttcccg atgtcctccg tgacgctatc ttaaattcct acaatgacgg tctgaccccc      1560
gtgattggca tgatggtgcc actggccatt gttgcaatgc tgatttttgtt cccactgcgc      1620 caagagcgct tgaaggaaac catcgaataa                                       1650
```

<210> SEQ ID NO 153
<211> LENGTH: 1650
<212> TYPE: DNA
<213> ORGANISM: Unknown
<220> FEATURE:
<223> OTHER INFORMATION: ImpE2 NT - V2I G64E

<400> SEQUENCE: 153

```
atgatagcta aaaactccac cccaagcacg gccggccacg ccagtgctca cactgcggaa       60
gaattcccag tggccaatgc tgaaatggca acgccttcag caatcgaccc aaaccacggt      120
aaaaagaccg cggataacgt cggcattatc ttcgctgcct tgatgctcac catgctgatg      180
agctctttgg agcagatgat tttcggttcc gctctgccaa ccatcgtcgg cgagctcggc      240
ggcgtggacc agatgagctg gtaatttca gcatttatgg tcaccatgac cattgctatg       300
ccactagccg gtcagctcgg tgaccgcatg ggccgcaagt gggtctacat ctcaggtatc      360
tccattttcg ttattggctc gacgctcggt ggctttgcca atggcatggg catgctgatc      420
accggacgtg caatccaggg cttcggtgcc ggcatcatga tgatttcctc gcagtcgatt      480
```

| | |
|---|---|
| gtggctgagg ttgtctccgc acgtgagcgc ggcaagttca tgggtattat gggcggcgtc | 540 |
| tttggcgtct cctccgtact gggtccagtt ctcggtggct ggttcaccga tggtcccggt | 600 |
| tggcgttggg gcctgtggat caacattcca ctgggtctgc tggcaattat tgtctgcgct | 660 |
| ttcgtactga agctgcgcgt gggcgagcaa ggctttaagg gctttgactg gatgggtttt | 720 |
| gcggccatcg caatcacgac cagcaccctg attctgctca ccacttgggg cggaagcgaa | 780 |
| tacgagtgga cttccccaac tattttgtcc atggctgccg tagtcatcgt cggcgcgctg | 840 |
| ctcaccgtgt tcattgagtc gcgtgcatcc cagccgctga tcccggttca gctatttaag | 900 |
| aaccgcaaca tggttttgac caccctcgcc ggtactgttt gggtctggc catgatgggc | 960 |
| gtgctcggct acatgccaac ctacctgcag atggtgcaca ccctgacgcc aactgaagca | 1020 |
| ggcttgatga tgatcccgat gatggtcggc atgatcggtg tctccactgg tgttggcttc | 1080 |
| atcatcgcta agaccggcaa ctacaagtac taccccatcg cgggcctggc catcacggcg | 1140 |
| tttgctttgt ggtggatgtc ccagatgacc gttgagactt cattgaccgg tatcggagtt | 1200 |
| cgcttccttg tattcggtgt cggcttgggc tttgtcatgc aggtactggt gctgattgtt | 1260 |
| caaaactcct tccctgtatc gcaggtcggt actgccacgg cggctaataa cttcttccgc | 1320 |
| cagattggtt cggcattggg tgcttccatc gtgggttcga tgttcattca caatatgcag | 1380 |
| aatgagatgg ctacccgttt gcctgatgcc cttgcatcgt tgggcaagga aggcgccgct | 1440 |
| atttcgcagc agttccaagg tgcagatgcc gccaactcct tgactccgca cgcagtcgca | 1500 |
| gagcttcccg atgtcctccg tgacgctatc ttaaattcct acaatgacgg tctgaccccc | 1560 |
| gtgattggca tgatggtgcc actggccatt gttgcaatgc tgattttgtt cccactgcgc | 1620 |
| caagagcgct tgaaggaaac catcgaataa | 1650 |

<210> SEQ ID NO 154
<211> LENGTH: 2312
<212> TYPE: DNA
<213> ORGANISM: Unknown
<220> FEATURE:
<223> OTHER INFORMATION: ImpE NT - CJI0323

<400> SEQUENCE: 154

| | |
|---|---|
| ttgcatgctg tgcaagaagt taatgacaat gaagaagact ccctccctgg cagtgacctc | 60 |
| gggttaaggg agcagaagcg attggcaacc aagcatcgca tcgaagacgc cgcgacacgg | 120 |
| ttggttgatg aatcgagctt tgacaaagta acaattgaag aaatttgcga agccgccggg | 180 |
| atttcccgac gcacctttt taattatttc agcacgaaag aaagcgccgt tattggcgcg | 240 |
| tcctcggaac cgttgacgga aaagcaacgc aatgacttct tgaatgctga cgccagcaat | 300 |
| ctcctgcagc tgatggttga gcagatcaaa caacacttgg agtcttctca ccagagtcaa | 360 |
| gcgattcacg accgtcgtca gcgaatcttt gcggatccgg atgtcgcggt acgtgcaatg | 420 |
| gcgtttcgca aggaacgctc acgggaaacc atggagctaa tcgctcaacg tcttcgggag | 480 |
| catcctgaaa acaacgcgc cccagaattg gatccggaaa cagaggcgat gctgctgagc | 540 |
| ggattcattc gcgaagccac ctggatggct atctcacgac ccgatcgtga ttgtgcactg | 600 |
| ccagtgggtg accgcatcta tcgcgcgatg gaattggtaa agaattacac gaaaggactg | 660 |
| gaatgatagc taaaaactcc accccaagca cggccggcca cgccagtgct cacactgcgg | 720 |
| aagaattccc agtggccaat gctgaaatgg caacgccttc agcaatcgac ccaaaccacg | 780 |
| gtaaaaagac cgcggataac gtcggcatta tcttcgctgc cttgatgctc accatgctga | 840 |

```
tgagctcttt ggagcagatg attttcggtt ccgctctgcc aaccatcgtc ggcgagctcg    900
gcggcgtgga ccagatgagc tgggtaattt cagcatttat ggtcaccatg accattgcta    960
tgccactagc cggtcagctc ggtgaccgca tgggccgcaa gtgggtctac atctcaggta   1020
tctccatttt cgttattggc tcgacgctcg gtggctttgc caatggcatg ggcatgctga   1080
tcaccggacg tgcaatccag ggcttcggtg ccggcatcat gatgatttcc tcgcagtcga   1140
ttgtggctga ggttgtctcc gcacgtgagc gcggcaagtt catgggtatt atgggcggcg   1200
tctttggcgt ctcctccgta ctgggtccag ttctcggtgg ctggttcacc gatggtcccg   1260
gttggcgttg gggcctgtgg atcaacattc cactgggtct gctggcaatt attgtctgcg   1320
ctttcgtact gaagctgcgc gtgggcgagc aaggctttaa gggctttgac tggatgggtt   1380
ttgcggccat cgcaatcacg accagcaccc tgattctgct caccacttgg ggcggaagcg   1440
aatacgagtg gacttcccca actatttttgt ccatggctgc cgtagtcatc gtcggcgcgc   1500
tgctcaccgt gttcattgag tcgcgtgcat cccagccgct gatcccggtt cagctattta   1560
agaaccgcaa catggttttg accaccctcg ccggtactgt tttgggtctg gccatgatgg   1620
gcgtgctcgg ctacatgcca acctacctgc agatggtgca caccctgacg ccaactgaag   1680
caggcttgat gatgatcccg atgatggtcg gcatgatcgg tgtctccact ggtgttggct   1740
tcatcatcgc taagaccggc aactacaagt actaccccat cgcgggcctg gccatcacgg   1800
cgtttgcttt gtggtggatg tcccagatga ccgttgagac ttcattgacc ggtatcggag   1860
ttcgcttcct tgtattcggt gtcggcttgg gctttgtcat gcaggtactg gtgctgattg   1920
ttcaaaactc cttccctgta tcgcaggtcg gtactgccac ggcggctaat aacttcttcc   1980
gccagattgg ttcggcattg ggtgcttcca tcgtgggttc gatgttcatt cacaatatgc   2040
agaatgagat ggctacccgt ttgcctgatg cccttgcatc gttgggcaag gaaggcgccg   2100
ctatttcgca gcagttccaa ggtgcagatg ccgccaactc cttgactccg cacgcagtcg   2160
cagagcttcc cgatgtcctc cgtgacgcta tcttaaattc ctacaatgac ggtctgaccc   2220
ccgtgattgg catgatggtg ccactggcca ttgttgcaat gctgattttg ttcccactgc   2280
gccaagagcg cttgaaggaa accatcgaat aa                                 2312
```